(12) United States Patent
Dugan

(10) Patent No.: US 11,033,822 B2
(45) Date of Patent: *Jun. 15, 2021

(54) SYSTEMS AND METHODS FOR IMPROVING FITNESS EQUIPMENT AND EXERCISE

(71) Applicant: Brian M. Dugan, Sleepy Hollow, NY (US)

(72) Inventor: Brian M. Dugan, Sleepy Hollow, NY (US)

(73) Assignee: Dugan Health, LLC, Sleepy Hollow, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/424,453

(22) Filed: May 28, 2019

(65) Prior Publication Data

US 2019/0275430 A1 Sep. 12, 2019

Related U.S. Application Data

(63) Continuation of application No. 15/628,640, filed on Jun. 20, 2017, now Pat. No. 10,300,388, which is a
(Continued)

(51) Int. Cl.
*A63F 13/65* (2014.01)
*A63F 13/24* (2014.01)
(Continued)

(52) U.S. Cl.
CPC ............ *A63F 13/65* (2014.09); *A63F 13/212* (2014.09); *A63F 13/24* (2014.09); *A63F 13/52* (2014.09);
(Continued)

(58) Field of Classification Search
CPC .............. A63F 2300/5553; A63F 13/65; A63F 2300/105; A63F 2300/1012;
(Continued)

(56) References Cited

U.S. PATENT DOCUMENTS 3,834,702 A 9/1974 Bliss
4,484,743 A 11/1984 Williams
(Continued)

FOREIGN PATENT DOCUMENTS

EP 1 292 217 B1 11/2005
EP 1 639 939 3/2006
(Continued)

OTHER PUBLICATIONS

Preliminary Amendment Submitted of U.S. Appl. No. 16/190,145, filed Aug. 28, 2019.
(Continued)

*Primary Examiner* — Steve Rowland
(74) *Attorney, Agent, or Firm* — Dugan & Dugan, PC

(57) ABSTRACT

The present invention provides systems for and methods of playing a video game that includes providing a game character having a virtual appearance characteristic, receiving an input signal indicative of a user exercise performance level, and altering the virtual appearance characteristic in response to receiving the input signal. Numerous other aspects are disclosed.

20 Claims, 10 Drawing Sheets

Related U.S. Application Data continuation of application No. 14/538,135, filed on Nov. 11, 2014, now Pat. No. 9,700,798, which is a continuation of application No. 11/692,185, filed on Mar. 27, 2007, now Pat. No. 8,939,831, which is a continuation-in-part of application No. 11/620,046, filed on Jan. 4, 2007, now abandoned, which is a continuation-in-part of application No. 10/094,396, filed on Mar. 8, 2002, now abandoned.

(60) Provisional application No. 60/786,810, filed on Mar. 27, 2006, provisional application No. 60/756,111, filed on Jan. 4, 2006, provisional application No. 60/274,306, filed on Mar. 8, 2001.

(51) Int. Cl.
*A63F 13/52* (2014.01)
*A63F 13/212* (2014.01)

(52) U.S. Cl.
CPC ..... *A63F 2300/204* (2013.01); *A63F 2300/66* (2013.01); *A63F 2300/69* (2013.01)

(58) Field of Classification Search
CPC ......... A63F 2300/65; A63F 2300/8005; G06F 19/3481; A63B 24/0062; A63B 69/32; A63B 2024/0096; A63B 2071/0638; A63B 24/0075
See application file for complete search history.

(56) References Cited

U.S. PATENT DOCUMENTS

| | | |
|---|---|---|
| 4,542,897 A | 9/1985 | Melton et al. |
| 4,735,410 A | 4/1988 | Nobuta |
| 4,817,938 A | 4/1989 | Nakao et al. |
| 4,858,930 A | 8/1989 | Sato |
| 4,976,435 A | 12/1990 | Shatford et al. |
| 5,001,632 A | 3/1991 | Hall-Tipping |
| 5,142,358 A | 8/1992 | Jason |
| 5,246,411 A | 9/1993 | Rackman |
| 5,318,487 A | 6/1994 | Golen et al. |
| RE34,728 E | 9/1994 | Hall-Tipping |
| 5,362,069 A | 11/1994 | Hall-Tipping |
| 5,377,100 A | 12/1994 | Pope et al. |
| 5,462,504 A | 10/1995 | Trulaske et al. |
| 5,515,865 A | 5/1996 | Scanlon |
| 5,527,239 A | 6/1996 | Abbondanza |
| 5,591,104 A | 1/1997 | Andrus et al. |
| 5,592,401 A | 1/1997 | Kramer |
| 5,624,316 A | 4/1997 | Roskowski et al. |
| 5,645,513 A | 7/1997 | Haydocy et al. |
| 5,667,459 A | 9/1997 | Su |
| 5,672,107 A | 9/1997 | Clayman |
| 5,702,323 A | 12/1997 | Poulton |
| 5,781,698 A | 7/1998 | Teller et al. |
| 5,839,990 A | 11/1998 | Virkkala |
| 5,885,156 A | 3/1999 | Toyohara et al. |
| 5,902,250 A | 5/1999 | Verrier et al. |
| 5,918,603 A | 7/1999 | Brown |
| 5,928,133 A | 7/1999 | Halyak |
| 5,947,868 A | 9/1999 | Dugan |
| 6,013,007 A | 1/2000 | Root et al. |
| 6,024,675 A | 2/2000 | Kashiwaguchi |
| 6,062,216 A | 5/2000 | Corn |
| 6,066,075 A | 5/2000 | Poulton |
| 6,152,856 A | 11/2000 | Studor et al. |
| 6,179,713 B1 | 1/2001 | James et al. |
| D439,981 S | 4/2001 | Kasabach et al. |
| 6,213,872 B1 | 4/2001 | Harada et al. |
| 6,217,449 B1 | 4/2001 | Kaku |
| 6,244,988 B1 | 6/2001 | Delman |
| 6,251,010 B1 | 6/2001 | Tajiri et al. |
| 6,267,677 B1 | 7/2001 | Tajiri et al. |
| 6,302,789 B2 | 10/2001 | Harada et al. |
| 6,321,158 B1 | 11/2001 | DeLorme et al. |
| D451,604 S | 12/2001 | Kasabach et al. |
| 6,347,993 B1 | 2/2002 | Kondo et al. |
| 6,354,940 B1 | 3/2002 | Itou et al. |
| 6,375,572 B1 | 4/2002 | Masuyama et al. |
| D460,971 S | 7/2002 | Sica et al. |
| 6,456,749 B1 | 9/2002 | Kasabach et al. |
| 6,482,092 B1 | 11/2002 | Tajiri et al. |
| 6,494,830 B1 | 12/2002 | Wessel |
| 6,513,160 B2 | 1/2003 | Dureau |
| 6,514,199 B1 | 2/2003 | Alessandri |
| 6,527,711 B1 | 3/2003 | Stivoric et al. |
| 6,579,231 B1 | 6/2003 | Phipps |
| 6,585,622 B1 | 7/2003 | Shum et al. |
| 6,595,858 B1 | 7/2003 | Tajiri et al. |
| 6,595,929 B2 | 7/2003 | Stivoric et al. |
| 6,601,016 B1 | 7/2003 | Brown et al. |
| 6,605,038 B1 | 8/2003 | Teller et al. |
| 6,628,847 B1 | 9/2003 | Kasabach et al. |
| 6,641,482 B2 | 11/2003 | Masuyama et al. |
| 6,652,383 B1 | 11/2003 | Sonoda et al. |
| 6,702,719 B1 | 3/2004 | Brown et al. |
| 6,705,972 B1 | 3/2004 | Takano et al. |
| 6,720,983 B1 | 4/2004 | Massaro et al. |
| 6,746,371 B1 | 6/2004 | Brown et al. |
| 6,758,746 B1 | 7/2004 | Hunter et al. |
| 6,786,825 B2 | 9/2004 | Kawazu |
| 6,796,927 B2 | 9/2004 | Toyama |
| 6,863,641 B1 | 3/2005 | Brown et al. |
| 6,881,176 B2 | 4/2005 | Oishi et al. |
| 6,888,779 B2 | 5/2005 | Mollicone et al. |
| 6,902,513 B1 | 6/2005 | McClure |
| 6,966,837 B1 | 11/2005 | Best |
| 7,020,508 B2 | 3/2006 | Stivoric et al. |
| 7,041,049 B1 | 5/2006 | Raniere |
| 7,057,551 B1 | 6/2006 | Vogt |
| 7,068,860 B2 | 6/2006 | Kasabach et al. |
| 7,077,751 B2 | 7/2006 | Nishiyama et al. |
| 7,153,262 B2 | 12/2006 | Stivoric et al. |
| 7,261,690 B2 | 8/2007 | Teller et al. |
| 7,285,090 B2 | 10/2007 | Stivoric et al. |
| 7,628,730 B1 | 12/2009 | Watterson et al. |
| 7,749,056 B2 | 7/2010 | Ando et al. |
| 7,789,800 B1 | 9/2010 | Watterson et al. |
| 7,837,595 B2 | 11/2010 | Rice |
| 7,931,563 B2 | 4/2011 | Shaw et al. |
| 7,934,983 B1 | 5/2011 | Eisner |
| 7,946,959 B2 | 5/2011 | Shum et al. |
| 8,188,868 B2 | 5/2012 | Case, Jr. |
| 8,287,383 B1 | 10/2012 | Etter et al. |
| 8,287,436 B2 | 10/2012 | Shum et al. |
| 8,292,743 B1 | 10/2012 | Etter et al. |
| 8,313,416 B2 | 11/2012 | Ellis et al. |
| 8,444,491 B2 | 5/2013 | Bethke et al. |
| 8,491,395 B2 | 7/2013 | Auterio et al. |
| 8,496,532 B1 | 7/2013 | Bethke et al. |
| 8,506,409 B2 | 8/2013 | Bethke et al. |
| 8,556,778 B1 | 10/2013 | Dugan |
| 8,608,570 B1 | 12/2013 | Mahajan et al. |
| 10,300,388 B2 * | 5/2019 | Dugan .................. A63F 13/52 |
| 2002/0019296 A1 | 2/2002 | Freeman |
| 2002/0019586 A1 | 2/2002 | Teller et al. |
| 2002/0022516 A1 | 2/2002 | Forden |
| 2002/0080035 A1 | 6/2002 | Youdenko |
| 2002/0082065 A1 | 6/2002 | Fogel et al. |
| 2002/0082077 A1 | 6/2002 | Johnson et al. |
| 2002/0090985 A1 | 7/2002 | Tochner et al. |
| 2002/0151992 A1 | 10/2002 | Hoffberg et al. |
| 2002/0160883 A1 | 10/2002 | Dugan |
| 2002/0163495 A1 | 11/2002 | Doynov |
| 2003/0224337 A1 | 12/2003 | Shum et al. |
| 2004/0023761 A1 | 2/2004 | Emery |
| 2004/0053690 A1 | 3/2004 | Fogel et al. |
| 2004/0127272 A1 | 7/2004 | Park et al. |
| 2004/0180708 A1 | 9/2004 | Southard et al. |
| 2005/0068169 A1 | 3/2005 | Copley et al. |
| 2005/0075214 A1 | 4/2005 | Brown |
| 2005/0101845 A1 | 5/2005 | Nihtila |

(56) References Cited

U.S. PATENT DOCUMENTS

| | | |
|---|---|---|
| 2005/0177051 A1 | 8/2005 | Almen |
| 2005/0227811 A1 | 10/2005 | Shum et al. |
| 2005/0275541 A1 | 12/2005 | Sengupta et al. |
| 2006/0025282 A1 | 2/2006 | Redmann |
| 2006/0031102 A1 | 2/2006 | Teller et al. |
| 2006/0040793 A1 | 2/2006 | Martens |
| 2006/0089543 A1 | 4/2006 | Kim et al. |
| 2006/0122474 A1 | 6/2006 | Teller et al. |
| 2006/0224051 A1 | 10/2006 | Teller et al. |
| 2006/0264730 A1 | 11/2006 | Stivoric et al. |
| 2006/0281543 A1 | 12/2006 | Sutton et al. |
| 2007/0004482 A1 | 1/2007 | Ando et al. |
| 2007/0038038 A1 | 2/2007 | Stivoric et al. |
| 2007/0053513 A1 | 3/2007 | Hoffberg |
| 2007/0111858 A1 | 5/2007 | Dugan |
| 2007/0167204 A1 | 7/2007 | Lyle et al. |
| 2007/0173705 A1 | 7/2007 | Teller et al. |
| 2007/0197274 A1 | 8/2007 | Dugan |
| 2007/0208233 A1 | 9/2007 | Kovacs |
| 2007/0239479 A1 | 10/2007 | Arrasvuori et al. |
| 2007/0260482 A1 | 11/2007 | Nurmela et al. |
| 2007/0265138 A1 | 11/2007 | Ashby |
| 2008/0027337 A1 | 1/2008 | Dugan et al. |
| 2008/0094226 A1 | 4/2008 | O'Shea et al. |
| 2008/0129518 A1 | 6/2008 | Carlton-Foss |
| 2008/0146892 A1 | 6/2008 | LeBoeuf et al. |
| 2008/0167861 A1 | 7/2008 | Inoue et al. |
| 2008/0191864 A1 | 8/2008 | Wolfson |
| 2008/0218310 A1 | 9/2008 | Alten et al. |
| 2008/0281633 A1 | 11/2008 | Burdea et al. |
| 2008/0318679 A1 | 12/2008 | Tran et al. |
| 2009/0005140 A1 | 1/2009 | Rose et al. |
| 2009/0121894 A1 | 5/2009 | Wilson et al. |
| 2009/0270743 A1 | 10/2009 | Dugan et al. |
| 2010/0033303 A1 | 2/2010 | Dugan et al. |
| 2010/0056340 A1 | 3/2010 | Ellis et al. |
| 2010/0160041 A1 | 6/2010 | Grant et al. |
| 2010/0240458 A1 | 9/2010 | Gaiba et al. |
| 2010/0287011 A1 | 11/2010 | Muchkaev |
| 2011/0065504 A1 | 3/2011 | Dugan et al. |
| 2011/0082008 A1 | 4/2011 | Cheung et al. |
| 2011/0190055 A1 | 8/2011 | Leyvand et al. |
| 2011/0260830 A1 | 10/2011 | Weising |
| 2011/0275483 A1 | 11/2011 | Dugan et al. |
| 2011/0312470 A1 | 12/2011 | Hickman |
| 2012/0208676 A1 | 8/2012 | Shum et al. |
| 2012/0252580 A1 | 10/2012 | Dugan |
| 2012/0253487 A1 | 10/2012 | Dugan |
| 2012/0253489 A1 | 10/2012 | Dugan |
| 2012/0306643 A1 | 12/2012 | Dugan |
| 2013/0006736 A1 | 1/2013 | Bethke et al. |
| 2013/0252731 A1 | 9/2013 | Dugan et al. |
| 2014/0011640 A1 | 1/2014 | Dugan |
| 2014/0155129 A1 | 6/2014 | Dugan |
| 2014/0309083 A1 | 10/2014 | Dugan |
| 2015/0065213 A1 | 3/2015 | Dugan |
| 2015/0151162 A1 | 6/2015 | Dugan |
| 2016/0151670 A1 | 6/2016 | Dugan |
| 2016/0317869 A1 | 11/2016 | Dugan |
| 2017/0106242 A1 | 4/2017 | Dugan |
| 2017/0282078 A1 | 10/2017 | Dugan |
| 2018/0200577 A1 | 7/2018 | Dugan |
| 2019/0076701 A1 | 3/2019 | Dugan |

FOREIGN PATENT DOCUMENTS

| | | |
|---|---|---|
| EP | 1 292 218 B1 | 4/2006 |
| EP | 1 702 560 | 9/2006 |
| EP | 1 743 571 A2 | 1/2007 |
| JP | 59-170173 | 9/1984 |
| JP | 08103568 | 4/1996 |
| WO | WO 96/05766 | 2/1996 |
| WO | WO 01/96986 A2 | 12/2001 |
| WO | WO 02/00111 | 1/2002 |
| WO | WO 02/078538 A2 | 10/2002 |
| WO | WO 03/015005 A2 | 2/2003 |
| WO | WO 2004/019172 A2 | 3/2004 |
| WO | WO 2004/032715 A2 | 4/2004 |
| WO | WO 2004/034221 A2 | 4/2004 |
| WO | WO 2005/016124 A2 | 2/2005 |
| WO | WO 2005/027720 A2 | 3/2005 |
| WO | WO 2005/029242 A2 | 3/2005 |
| WO | WO 2005/092177 | 10/2005 |

OTHER PUBLICATIONS

Preliminary Amendment Submitted of U.S. Appl. No. 16/190,145, filed Sep. 17, 2019.
Preliminary Amendment Submitted of U.S. Appl. No. 16/190,145, filed Sep. 18, 2019.
Busch, Fritz "Diabetes Institute Brings Dakota, New Ulm Together" Jun. 10, 2001. Ogden Newspapers, Inc.
"Bluetooth." Wikipedia: The Free Encyclopedia. Aug. 10, 2009 <http://en.wikipedia.org/wiki/Bluetooth>.
Ichinoseki-sekine et al., "Improving the Accuracy of Pedometer Used by the Elderly with the FFT Algorithm," Medicine & Science in Sports & Exercise 2006,1674-1681.
Mann, W. et al., "Smart Phones for the Elders: Boosting the Intelligence of Smart Homes," Am. Assoc. for Artificial Intell., (AAAI), Jul. 2002.
Office Action of U.S. Appl. No. 11/692,185 dated Mar. 12, 2014.
Preliminary Amendment of U.S. Appl. No. 10/094,396 dated May 20, 2002.
Office Action of U.S. Appl. No. 10/094,396 dated Oct. 4, 2004.
Mar. 4, 2005 Response to Office Action of U.S. Appl. No. 10/094,396 dated Oct. 4, 2004.
Final Office Action of U.S. Appl. No. 10/094,396 dated Jun. 2, 2005.
Nov. 2, 2005 Response to Final Office Action & RCE of U.S. Appl. No. 10/094,396 dated Jun. 2, 2005.
Office Action of U.S. Appl. No. 10/094,396 dated Feb. 9, 2006.
Aug. 9, 2006 Response to Office Action of U.S. Appl. No. 10/094,396 dated Feb. 9, 2006.
Office Action of U.S. Appl. No. 10/094,396 dated May 4, 2007.
Oct. 4, 2007 Response to Office Action of U.S. Appl. No. 10/094,396 dated May 4, 2007.
Office Action of U.S. Appl. No. 10/094,396 dated Jan. 25, 2008.
Jul. 25, 2008 Response to Office Action of U.S. Appl. No. 10/094,396 dated Jan. 25, 2008.
Final Office Action of U.S. Appl. No. 10/094,396 dated May 13, 2009.
Office Action of U.S. Appl. No. 10/094,396 dated Apr. 14, 2010.
Jul. 14, 2010 Response to Office Action of U.S. Appl. No. 10/094,396 dated Apr. 14, 2010.
Restriction Requirement of U.S. Appl. No. 10/094,396 dated May 4, 2004.
Jul. 2, 2004 Response to Restriction Requirement of U.S. Appl. No. 10/094,396 dated May 4, 2004.
Interview Summary of U.S. Appl. No. 10/094,396 filed Nov. 7, 2005.
Restriction Requirement and Examiner Interview Summary of U.S. Appl. No. 10/094,396 dated Oct. 31, 2006.
Jan. 31, 2007 Response to Restriction Requirement of U.S. Appl. No. 10/094,396 dated Oct. 31, 2006.
Final Office Action of U.S. Appl. No. 10/094,396 dated Oct. 14, 2010.
Notice of Abandonment of U.S. Appl. No. 10/094,396 dated Oct. 21, 2011.
Appeal Brief of U.S. Appl. No. 10/094,396, filed Dec. 14, 2009.
Office Action of U.S. Appl. No. 11/620,046 dated Nov. 12, 2009.
Feb. 12, 2010 Response to Office Action of U.S. Appl. No. 11/620,046 dated Nov. 12, 2009.
Final Office Action of U.S. Appl. No. 11/620,046 dated Jun. 23, 2010.
Restriction Requirement of U.S. Appl. No. 11/620,046 dated Jun. 23, 2009.
Jul. 24, 2009 Response to Restriction Requirement of U.S. Appl. No. 11/620,046 dated Jun. 23, 2009.

(56) References Cited

OTHER PUBLICATIONS

Notice of Abandonment of U.S. Appl. No. 11/620,046 dated Jan. 21, 2011.
Office Action of U.S. Appl. No. 11/692,185 dated Oct. 7, 2009.
Jan. 7, 2010 Response to Office Action of U.S. Appl. No. 11/692,185 dated Oct. 7, 2009.
Final Office Action of U.S. Appl. No. 11/692,185 dated Mar. 3, 2010.
Appeal Brief of U.S. Appl. No. 11/692,185 mailed Jun. 3, 2010.
Examiner Interview Summary of U.S. Appl. No. 11/692,185 dated Jan. 15, 2010.
Interview Summary of U.S. Appl. No. 11/692,185, filed Jan. 26, 2010.
Interview Summary of U.S. Appl. No. 11/692,185, filed Feb. 3, 2010.
Examiner Answer of U.S. Appl. No. 11/692,185 dated Sep. 22, 2010.
Reply Brief of U.S. Appl. No. 11/692,185, filed Nov. 22, 2010.
Decision on Appeal of U.S. Appl. No. 11/692,185 mailed Dec. 13, 2013.
Office Action of U.S. Appl. No. 13/183,405 dated Apr. 30, 2012.
Oct. 28, 2012 Response to Apr. 30, 2012 Office Action of U.S. Appl. No. 13/183,405.
Final Office Action of U.S. Appl. No. 13/183,405 dated Mar. 25, 2013.
Jun. 3, 2013 Reply to Mar. 25, 2013 Final Office Action of U.S. Appl. No. 13/183,405.
Notice of Allowance of U.S. Appl. No. 13/183,405 dated Jun. 25, 2013.
Notice of Allowance of U.S. Appl. No. 13/942,605 dated Sep. 3, 2013.
Notice of Allowance of U.S. Appl. No. 14/023,892 dated Oct. 30, 2013.
Notice of Allowance of U.S. Appl. No. 14/172,859 dated Mar. 14, 2014.
Jun. 12, 2014 Reply to Mar. 12, 2014 Office Action of U.S. Appl. No. 11/692,185.
Examiner Interview Summary of U.S. Appl. No. 11/692,185 dated Jun. 16, 2014.
Preliminary Amendment of U.S. Appl. No. 14/313,995 filed Jul. 15, 2014.
Notice of Allowance of U.S. Appl. No. 11/692,185 dated Sep. 12, 2014.
Notice of Allowance & Examiner Interview Summary of U.S. Appl. No. 14/313,995 dated Oct. 28, 2014.
Amendment After Allowance Under 37 C.F.R. §1.312 of U.S. Appl. No. 14/313,995 filed Nov. 10, 2014.
Supplemental Notice of Allowability of U.S. Appl. No. 14/313,995 dated Nov. 21, 2014.
Non-Final Office Action of U.S. Appl. No. 14/538,135 dated Dec. 22, 2015.
Non-Final Office Action of U.S. Appl. No. 14/619,064 dated Mar. 16, 2015.
Sep. 16, 2015 Reply and Terminal Disclaimer to Mar. 16, 2015 Non-Final Office Action of U.S. Appl. No. 14/619,064.
Notice of Allowance of U.S. Appl. No. 14/619,064 dated Oct. 15, 2015.
Preliminary Amendment and Terminal Disclaimer of U.S. Appl. No. 15/017,562 filed Mar. 7, 2016.
Preliminary Amendment of U.S. Appl. No. 15/017,562, filed Mar. 9, 2016.
Notice of Allowance and Applicant-Initiated Interview Summary of U.S. Appl. No. 15/017,562 dated Apr. 6, 2016.
May 23, 2016 Reply to Dec. 22, 2015 Non-Final Office Action of U.S. Appl. No. 14/538,135.
Supplemental Amendment of U.S. Appl. No. 14/538,135, filed Jun. 23, 2016.
Applicant-Initiated Interview Summary of U.S. Appl. No. 14/538,135 dated Jun. 27, 2016.
Applicant-Initiated Interview Summary of U.S. Appl. No. 14/538,135 dated Jun. 12, 2016.
Final Office Action of U.S. Appl. No. 14/538,135 dated Sep. 1, 2016.
Notice of Allowance of U.S. Appl. No. 15/208,598 dated Sep. 28, 2016.
Amendment After Allowance Rule 312 of U.S. Appl. No. 15/208,598, filed Dec. 28, 2016.
Response to Rule 312 Communication of U.S. Appl. No. 15/208,598 dated Jan. 17, 2017.
Examiner Interview Summary of U.S. Appl. No. 14/538,135, filed Mar. 1, 2017.
Notice of Allowance and Applicant-Initiated Interview Summary of U.S. Appl. No. 14/538,135 dated Mar. 10, 2017.
Non-Final Office Action of U.S. Appl. No. 15/393,247 dated Jun. 6, 2017.
Nov. 6, 2017 Reply and Terminal Disclaimer to Jun. 6, 2017 Non-Final Office Action of U.S. Appl. No. 15/393,247.
Notice of Allowance of U.S. Appl. No. 15/393,247 dated Nov. 29, 2017.
Amendment After Notice of Allowance (Rule 312) of U.S. Appl. No. 15/393,247, filed Feb. 27, 2018.
Response to Rule 312 Communication of U.S. Appl. No. 15/393,247 dated Mar. 8, 2018.
Non-Final Office Action of U.S. Appl. No. 15/628,640 dated Jun. 7, 2018.
Notice of Allowance of U.S. Appl. No. 15/920,449 dated Aug. 9, 2018.
Dec. 7, 2018 Reply to Non-Final Office Action and Terminal Disclaimer of U.S. Appl. No. 15/628,640.
Notice of Allowance of U.S. Appl. No. 15/628,640 dated Jan. 15, 2019.
Dugan, U.S. Appl. No. 16/392,612, titled: "Systems and Methods for Improving Fitness Equipment and Exercise," filed Apr. 23, 2019.
Non-Final Office Action of U.S. Appl. No. 16/392,612 dated Jun. 25, 2020.

* cited by examiner

SYSTEMS AND METHODS FOR IMPROVING FITNESS EQUIPMENT AND EXERCISE

CROSS-REFERENCE TO RELATED APPLICATIONS

This application is a continuation of and claims priority to U.S. patent application Ser. No. 15/628,640 filed Jun. 20, 2017, now U.S. Pat. No. 10,300,388, and entitled "SYSTEMS AND METHODS FOR IMPROVING FITNESS EQUIPMENT AND EXERCISE", which is a continuation of and claims priority to U.S. patent application Ser. No. 14/538,135 filed Nov. 11, 2014, now U.S. Pat. No. 9,700,798, and entitled "SYSTEMS AND METHODS FOR IMPROVING FITNESS EQUIPMENT AND EXERCISE", which is a continuation of and claims priority to U.S. patent application Ser. No. 11/692,185 filed Mar. 27, 2007, now U.S. Pat. No. 8,939,831, and entitled "SYSTEMS AND METHODS FOR IMPROVING FITNESS EQUIPMENT AND EXERCISE", which claims priority to U.S. Provisional Patent Application Ser. No. 60/786,810, filed Mar. 27, 2006, and entitled "SYSTEMS AND METHODS FOR IMPROVING FITNESS EQUIPMENT AND EXERCISE,", and which is a continuation-in-part of U.S. patent application Ser. No. 11/620,046, filed Jan. 4, 2007, and entitled "SYSTEMS AND METHODS FOR USING A VIDEO GAME TO ACHIEVE AN EXERCISE OBJECTIVE," which claims priority to U.S. Provisional Patent Application Ser. No. 60/756,111, filed Jan. 4, 2006, and entitled "SYSTEMS AND METHODS FOR IMPROVING FITNESS EQUIPMENT AND EXERCISE," and which is a continuation-in-part of U.S. patent application Ser. No. 10/094,396, filed Mar. 8, 2002, and entitled "SYSTEM AND METHOD FOR IMPROVING FITNESS EQUIPMENT AND EXERCISE," which claims priority to U.S. Provisional Patent Application Ser. No. 60/274,306, filed Mar. 8, 2001, and entitled "INTERNET-BASED APPOINTMENT SCHEDULING,". All of the above patent applications are hereby incorporated by reference herein in their entirety.

FIELD OF THE INVENTION

The present invention relates to exercise equipment and fitness activities, and more particularly to systems and methods for improving fitness equipment and exercise.

BACKGROUND OF THE INVENTION

A fitness craze has recently swept the United States and many other countries. From fat-free potato chips to treadmills, people around the world have become obsessed with weight loss and healthy living. Accordingly, record numbers of new fitness products/exercise equipment have emerged to meet this obsession (including stair climbers, treadmills, recumbent bicycles, ski machines, and the like).

Many pieces of exercise equipment, when used regularly, are very useful for weight loss, for improving cardiovascular stamina, and for strengthening various muscles. However, most exercise equipment suffers from a major drawback: the equipment is boring to use because of its inability to successfully encourage a user (e.g., an exerciser) to continue exercising. As a result, most purchasers of exercise equipment stop using the equipment shortly after purchasing it.

A need therefore exists for a system and a method for making both existing and new exercise equipment more enjoyable by successfully stimulating and encouraging an exerciser to continue exercising. Such a system and a method will significantly improve both existing and new exercise equipment, as well as exercise itself (e.g., by making it more enjoyable).

U.S. Pat. No. 5,947,868 (the '868 Patent) discloses, among other things, a system and method for improving fitness equipment and exercise. This patent is hereby incorporated by reference herein in its entirety. In one embodiment of the '868 Patent, a monitor measures a performance level of an exerciser and outputs a performance level signal to a video game player (e.g., a hand-held video game player such as a Gameboy™ manufactured by Nintendo). The video game player monitors the performance level signal and controls the performance level of a video game character based on the signal. Additional methods and apparatus for encouraging or otherwise regulating exercise would also be desirable.

SUMMARY

In some aspects, the present invention provides a method of playing a video game that includes providing a game character having a virtual appearance characteristic; receiving an input signal indicative of a user exercise performance level; and altering the virtual appearance characteristic in response to receiving the input signal.

In some other aspects, the present invention provides a method of playing a video game that includes providing a game character having a virtual appearance characteristic; receiving an input signal indicative of achievement of a physical goal by a user; and altering the virtual appearance characteristic in response to receiving the input signal.

In yet other aspects, the present invention provides a system for playing a video game that includes a game system adapted to allow a user to interact with a virtual environment using a game character having a virtual appearance characteristic; an input device coupled to the game system and adapted to provide an input signal to the game system indicative of an exercise performance level of the user; and a game adapted to execute on the game system and further adapted to alter the virtual appearance characteristic in response to receiving the input signal.

In still yet other aspects, the present invention provides a video game that includes code adapted to allow a user to interact with a virtual environment using a game character having a virtual appearance characteristic; an input device coupled to a game system adapted to execute the code, wherein the input device is adapted to provide an input signal to the game system indicative of an exercise performance level of the user; and further code adapted to execute on the game system and further adapted to alter the virtual appearance characteristic in response to receiving the input signal.

Other features and aspects of the present invention will become more fully apparent from the following detailed description, the appended claims, and the accompanying drawings.

No. 5,947,868 (modified to include software and/or databases to implement the methods described below).

Figure 3:
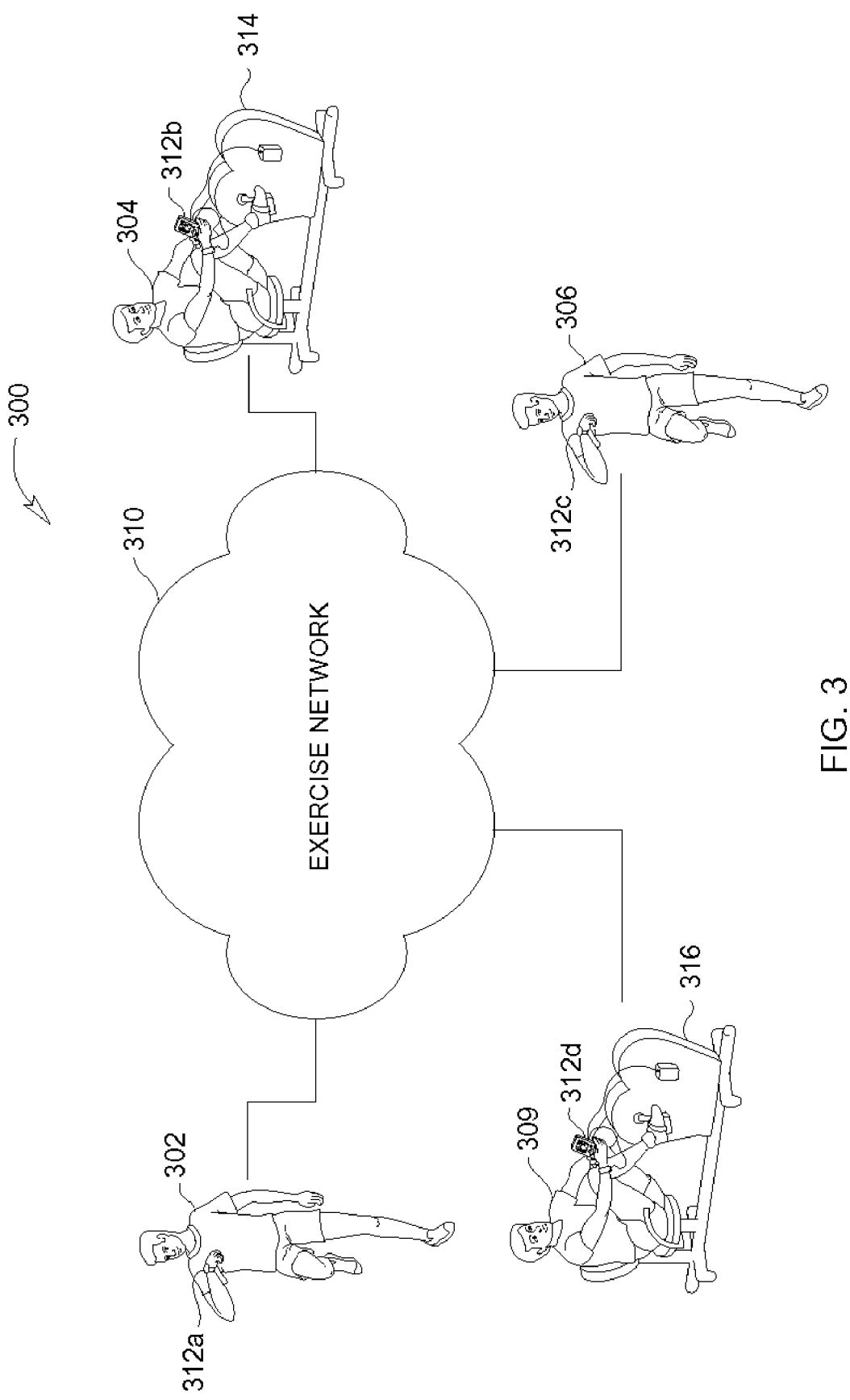

FIG. 3 is a schematic view of an exercise network according to embodiments of the present invention.

FIGS. 4A-D illustrate various transformations that a video game character may undergo in response to exercise performance levels in some embodiments of the present invention.

Figure 5:
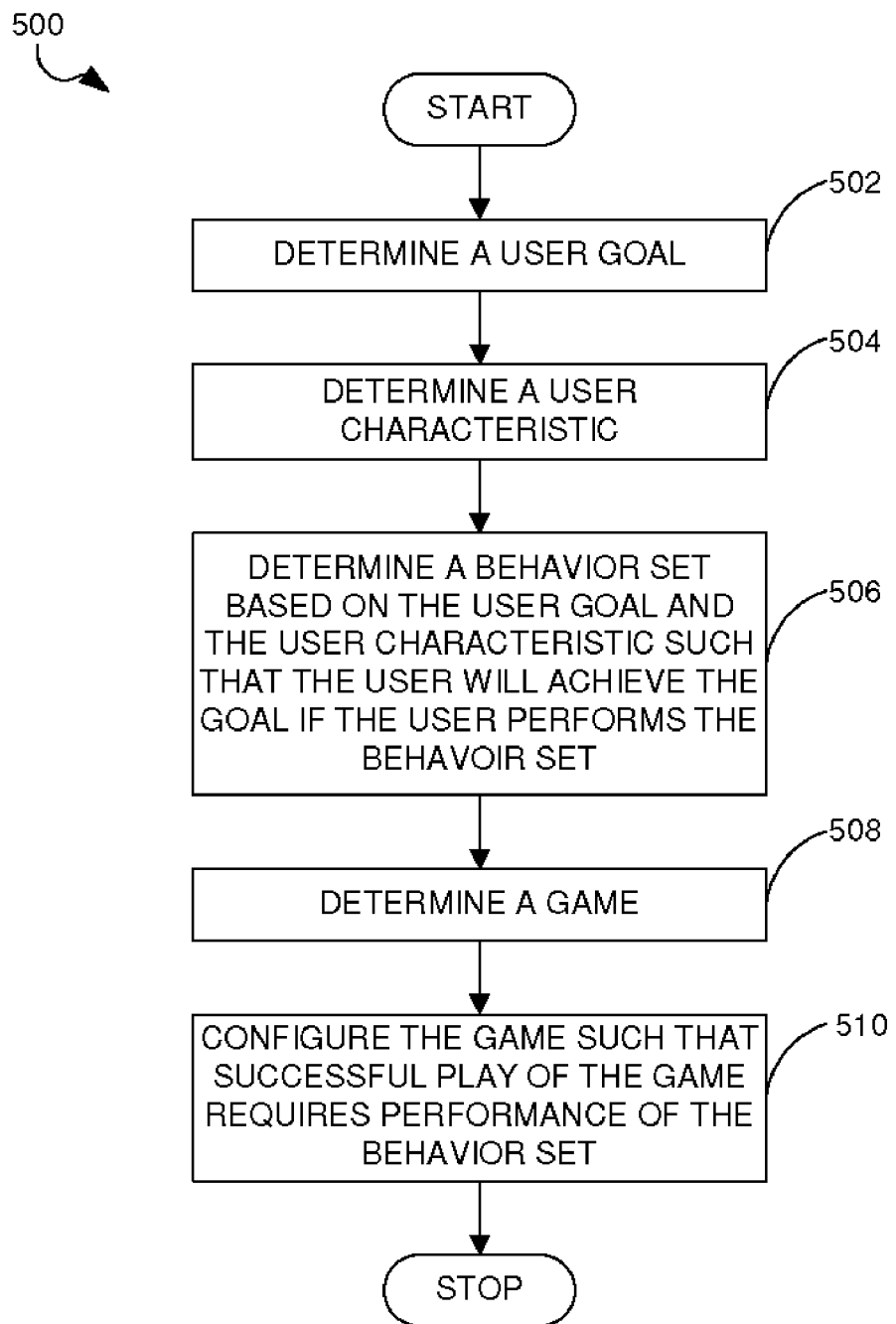

FIG. 5 is a flowchart of a first exemplary method provided in accordance with the present invention.

Figure 6:
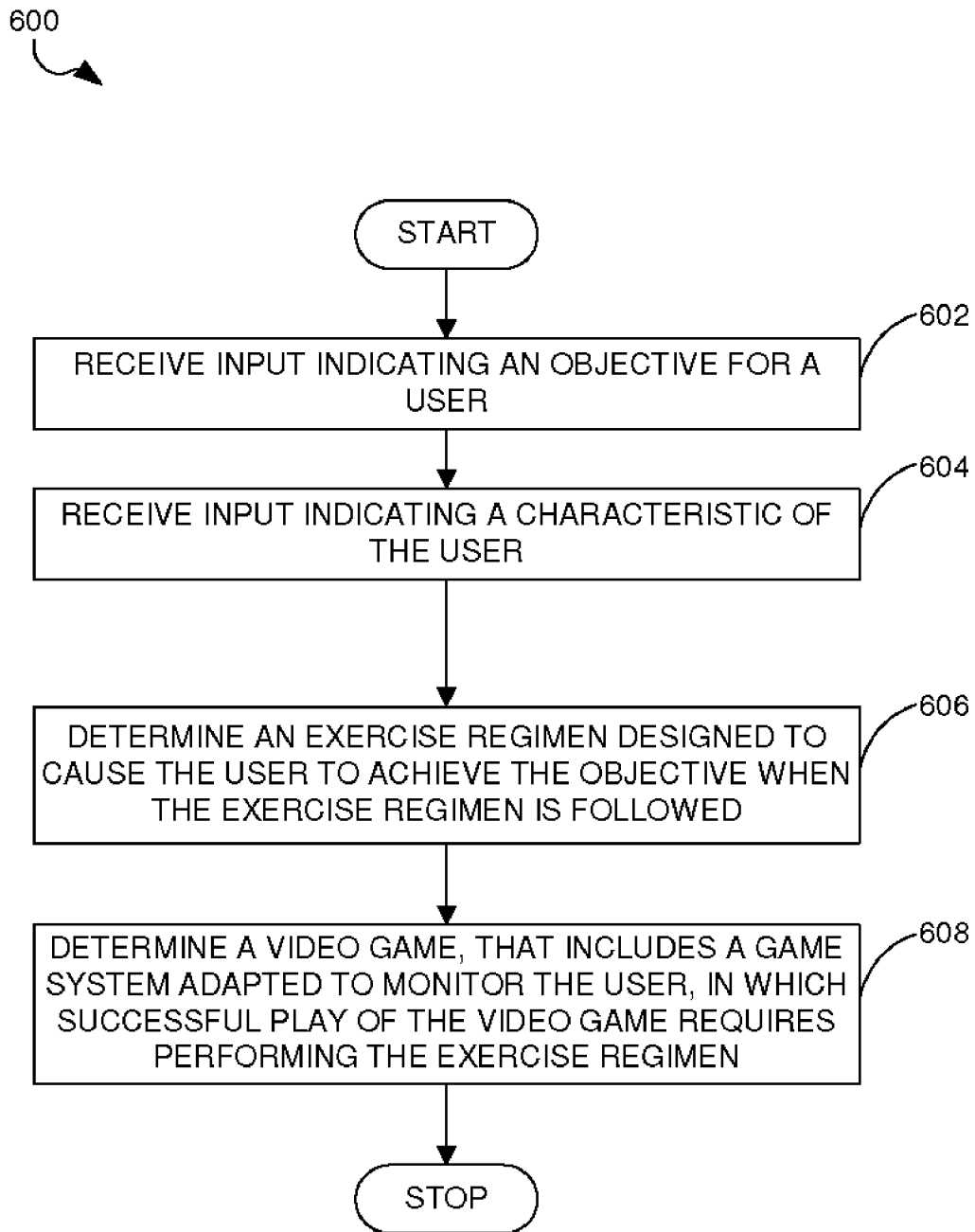

FIG. 6 is a flowchart of a second exemplary method provided in accordance with the present invention.

Figure 7:
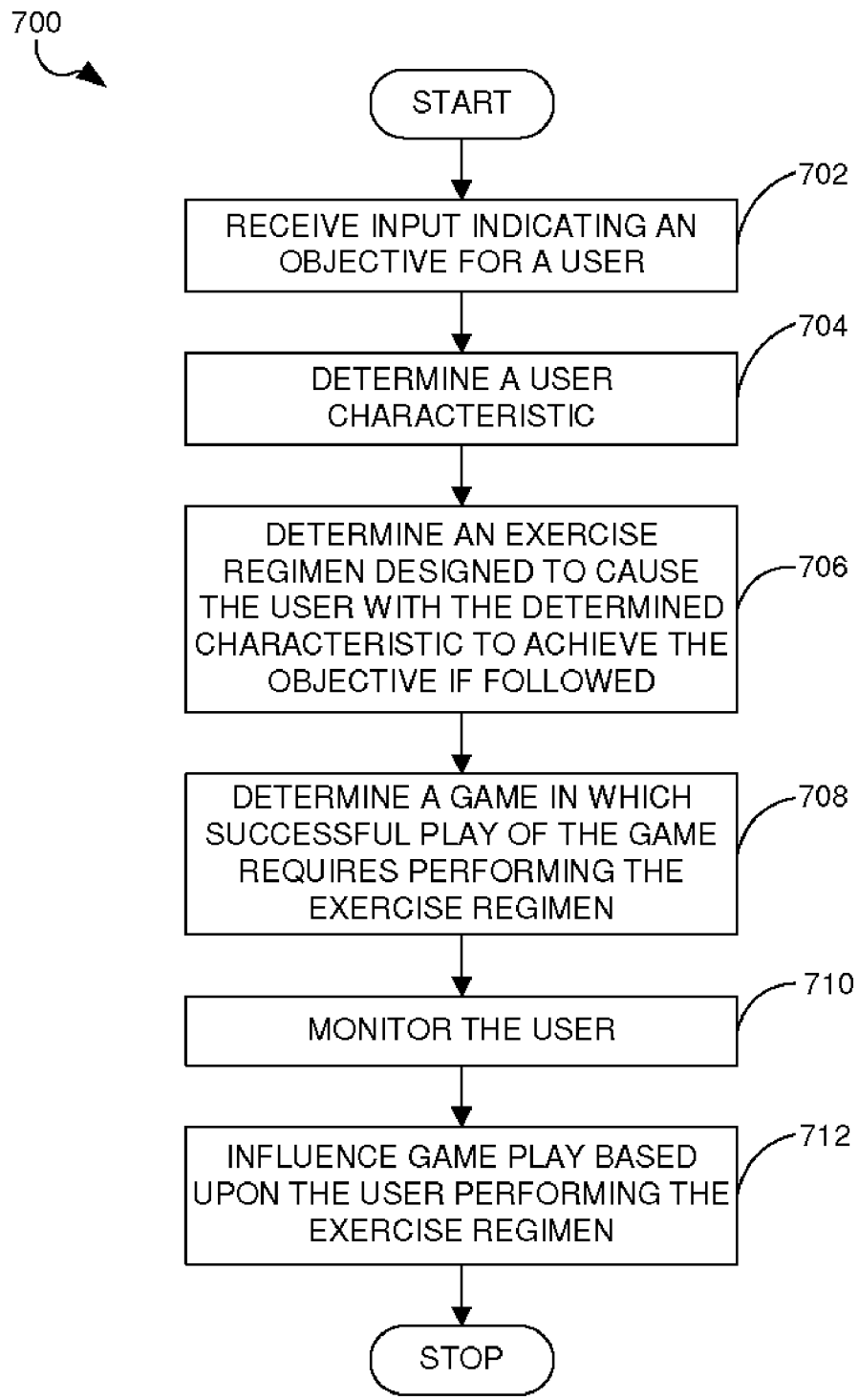

FIG. 7 is a flowchart of a third exemplary method provided in accordance with the present invention.

Figure 8:
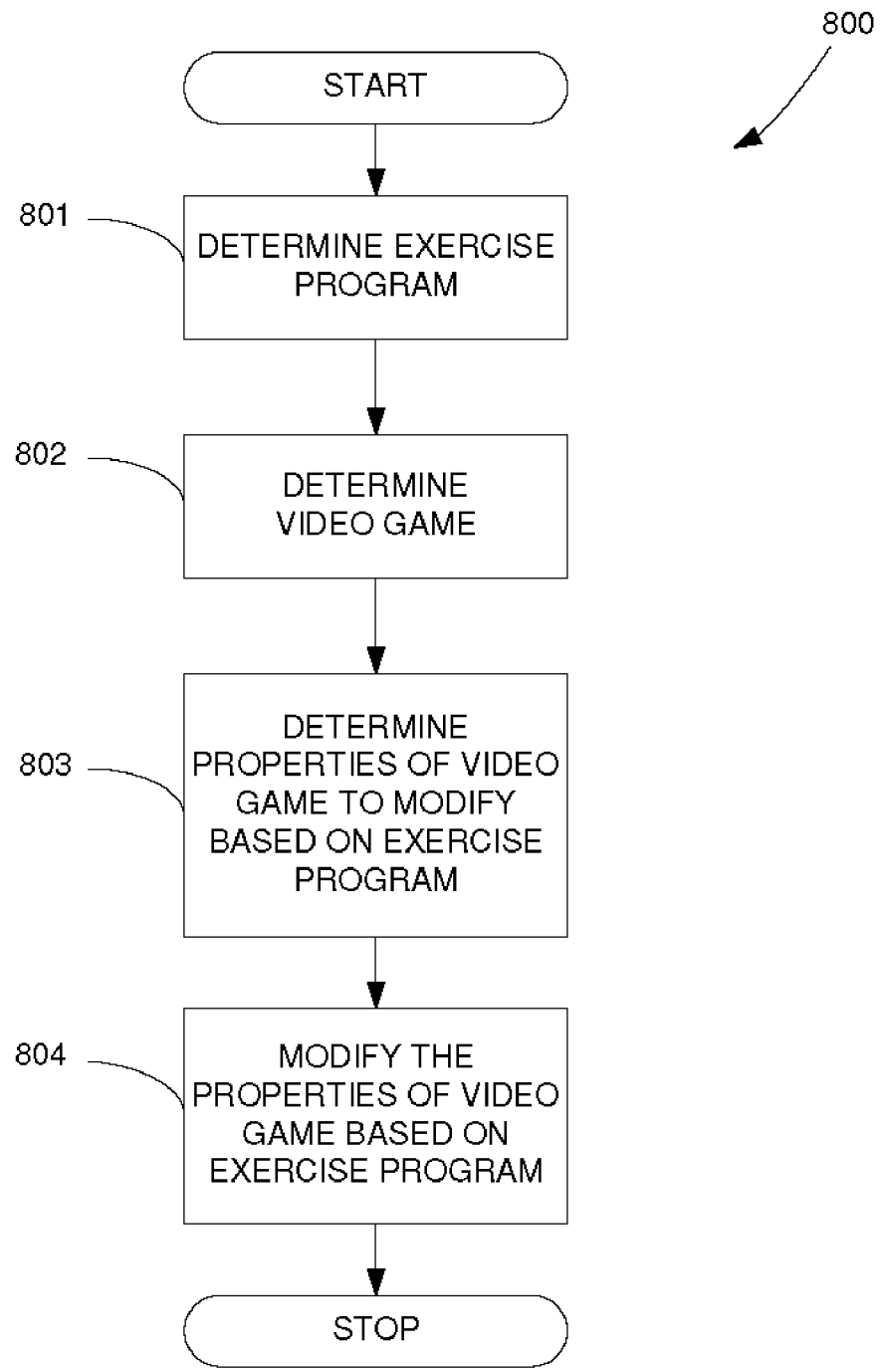

FIG. 8 is a flowchart of a fourth exemplary method provided in accordance with the present invention.

Figure 9:
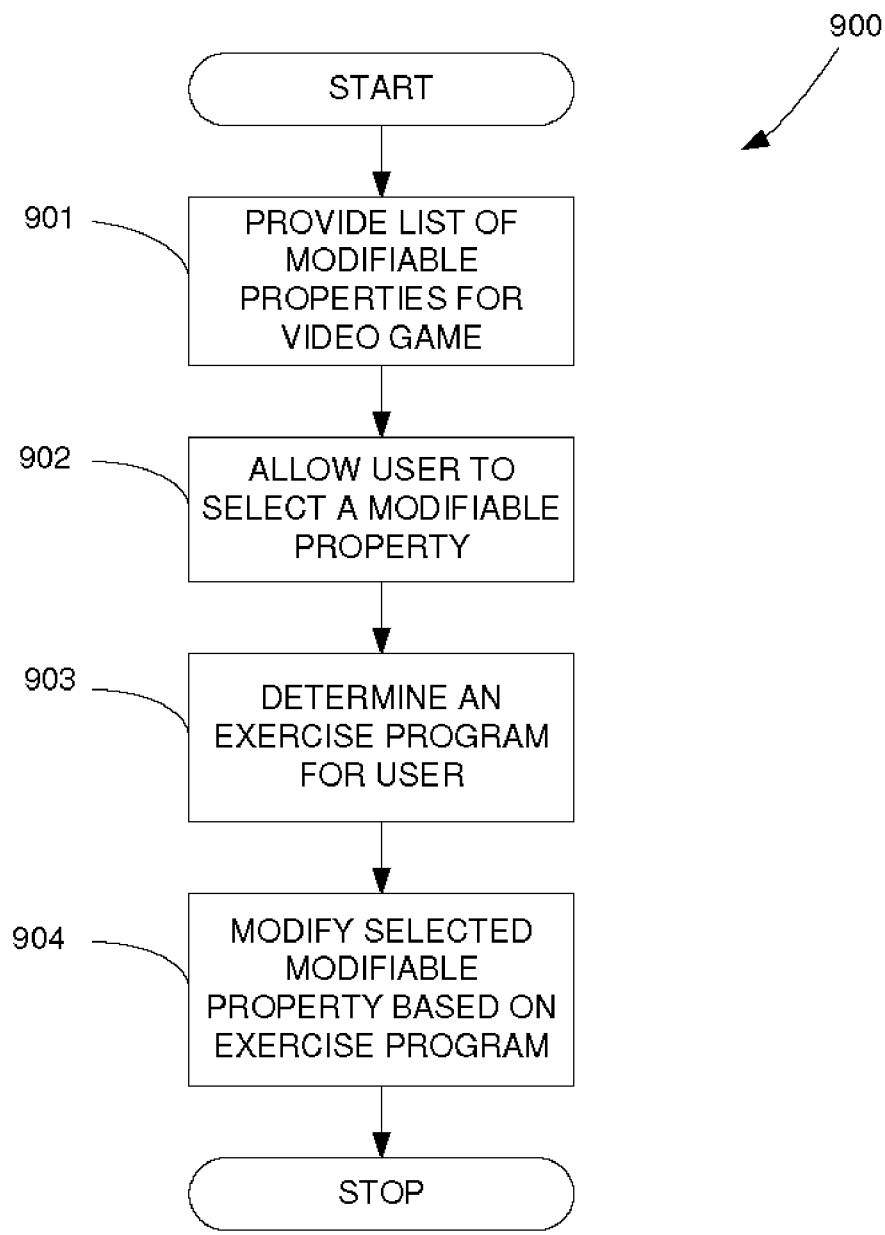

FIG. 9 is a flowchart of a fifth exemplary method provided in accordance with the present invention.

Figure 10:
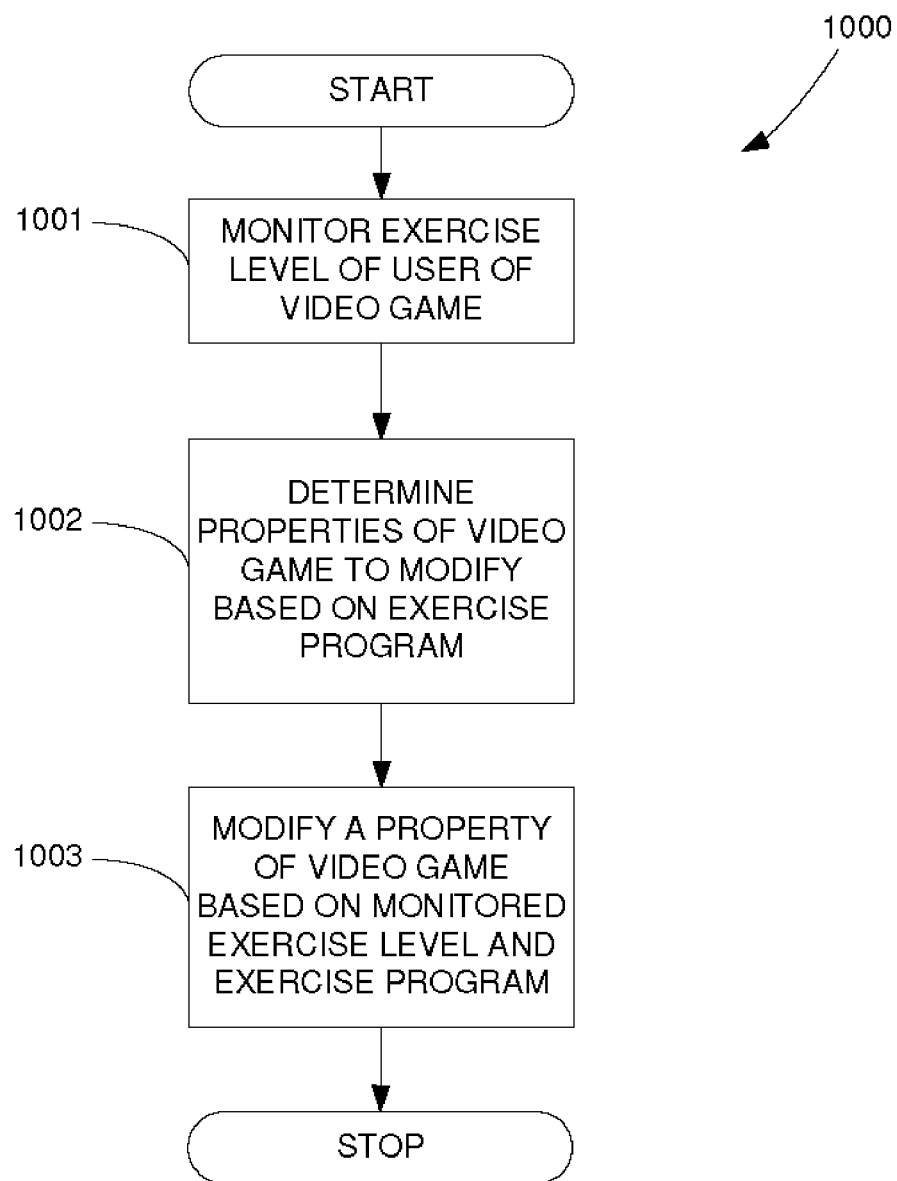

FIG. 10 is a flowchart of an sixth exemplary method provided in accordance with the present invention.

DETAILED DESCRIPTION

Figure 1:
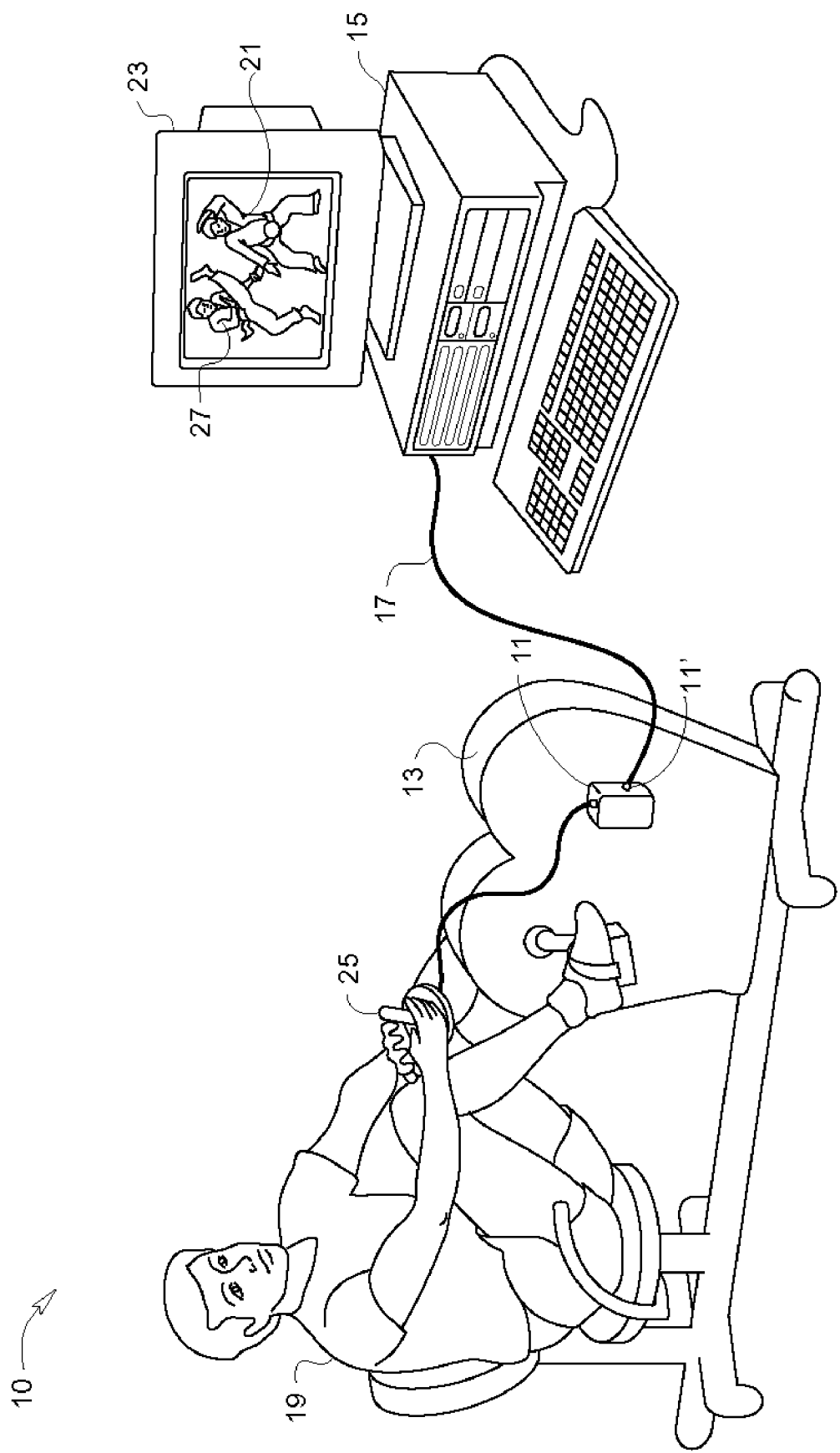
FIG. 1 is a schematic view of an exercise system configured in accordance with a first embodiment of U.S. Pat. No. 5,947,868 (modified to include software and/or databases to implement the methods described below).

To further aid in the understanding of the present invention, the exercise system of U.S. Pat. No. 5,947,868 will be described herein. Specifically, FIG. 1 is a schematic view of an exercise system 10 configured in accordance with a first embodiment of U.S. Pat. No. 5,947,868. With reference to FIG. 1, the exercise system 10 comprises an exercise monitor 11 connected to a recumbent bicycle 13, and a computer 15 coupled to an output 11' of the exercise monitor 11 via a cable 17. Any other piece of exercise equipment may be similarly employed (e.g., a stair climber, a stationary bicycle, a rowing machine, etc.).

The exercise monitor 11 is configured to measure the pedal rate of an exerciser 19 riding the recumbent bicycle 13, and to output an approximately real-time measure of pedal rate via the output 11'. Other or additional exerciser performance levels (e.g., a measure of the length, intensity or some other characteristic of the exercise activity) may be monitored and output by monitor 11 or by other monitors. The pedal rate output by the monitor 11 is monitored by the computer 15 while the computer 15 runs a video game such as a martial arts video game (represented in FIG. 1 by a martial arts character 21 on a computer screen 23 coupled to the computer 15).

The exerciser 19 is shown holding a joystick 25 for controlling the kicking, punching and other movements of the martial arts character 21 on the computer screen 23. The joystick 25 may be directed connected to the computer 15 or coupled to the computer 15 via the monitor 11 as shown in FIG. 1. The joystick/computer connection also may be wireless.

In operation, as the exerciser 19 pedals the recumbent bicycle 13, the monitor 11 measures and outputs (via the output 11') a signal representative of the pedal rate of the exerciser 19. The pedal rate signal output by the monitor 11 is monitored by the computer 15 and is used to control the energy level (e.g., the strength and durability) of the martial arts character 21. Accordingly, the harder the exerciser 19 pedals the bicycle 13, the higher the energy level of the martial arts character 21, and the less likely the martial arts character 21 is to perish from an attack by an opponent martial arts character 27. By exercising harder, the exerciser 19 can therefore score higher or otherwise perform better at the video game.

Many different performance levels of the exerciser 19 can be monitored and used to control a video game character's performance levels (e.g., how the character behaves, reacts, etc.). Table 1 contains a representative list of exerciser performance levels that may be monitored as the exerciser 19 exercises on the recumbent bicycle 13 or on some other piece of exercise equipment, and possible video character performance levels that can be controlled for each monitored exerciser performance level. Table 1 is not intended as a limitation on monitorable performance levels and is merely exemplary.

TABLE 1

| MONITORED EXERCISER PERFORMANCE LEVEL | VIDEO GAME CHARACTER PERFORMANCE LEVEL CONTROLLED |
|---|---|
| pedaling rate | speed, striking force |
| stepping rate | speed, striking force |
| rowing rate | speed, striking force |
| running rate | speed, striking force |
| pulse rate | speed, energy level, accuracy |
| striking force | striking force |
| swing velocity | swing velocity |
| distance traveled | game level |
| time exercised | game level |

Accordingly, exercise equipment, such as the recumbent bicycle 13, and/or exercise is modified by placing an exercise monitor 11 (e.g., a pulse monitor, a distance meter, a rate monitor, a time monitor, a calorie meter, a strain gauge, an accelerometer and/or any other sensor for measuring the physical activity/performance level of an exerciser) on the equipment and/or the exerciser 19. The exercise monitor 11 outputs a signal representative of the performance level of the exerciser 19 (e.g., pulse rate, distance traveled, time exercised, rate of exercise, etc.) to a video game player (e.g., a computer 15) wirelessly or via a cable. The video game player may be a desk top computer, or preferably comprises a hand-held video game player such as a GameBoy™ (as described with reference to FIG. 2).

To stimulate the exerciser 19, the output from the exercise monitor 11 is used to control a parameter within a video game, such as a video game character 21's lifetime, energy level, striking force, accuracy, speed or the like. Similarly, a video game character 21 may be precluded from reaching a higher level in a game unless the exerciser 19 pedals fast enough, exercises long enough, has a high (or low) enough pulse rate or reaches some other performance level. Multiple performance level measurements of the exerciser 19 may be monitored and used to control multiple performance levels of the video game character 21 (e.g., pulse rate of the exerciser 19 dictates energy level/lifetime of the video game character 21, exercise rate controls the speed of or the striking force of the video game character 21, and duration/distance of exercise controls game level).

Examples of suitable video games include action-adventure games (e.g., military games, dungeon games, murder-mystery games, etc.), martial arts games, sports games (e.g., hiking, swimming, baseball, basketball, tennis, etc.), and other similar games. For instance, during a video baseball game, the force with which a batter strikes a baseball or the speed with which a player runs around a base may be controlled by the speed with which an exerciser pedals, climbs stairs, rows, etc. Similarly, the speed with which a football player rushes or passes, the power with which a boxer punches or a martial artist kicks, or the height to which a basketball player jumps may be similarly controlled. The "energy level" (e.g., a measure of how long a character can survive an event, attack, etc.) or lifetime of a character can be similarly controlled, or controlled by the pulse rate or other cardiovascular indicator of the exerciser. The key is to make the exerciser exercise harder or longer in order to continue the game or do better in the game. Accordingly, the exerciser is stimulated to work harder in exchange for some immediate success or gratification (e.g., doing better in the game). Preferably, game score/performance will increase with an increasing level of physical fitness (e.g., reduced pulse rate for a given exercise routine, harder workouts, etc.).

If desired, the video game player may analyze the data from the exercise monitor and compile statistics on the exerciser's performance. A database can be maintained for each new exerciser and updated after each exercise session so that progress charts and other statistics can be generated for each exerciser. If desired, other relevant data such as an exerciser's weight, body fat, and the like also may be stored and used to assess progress.

Figure 2:
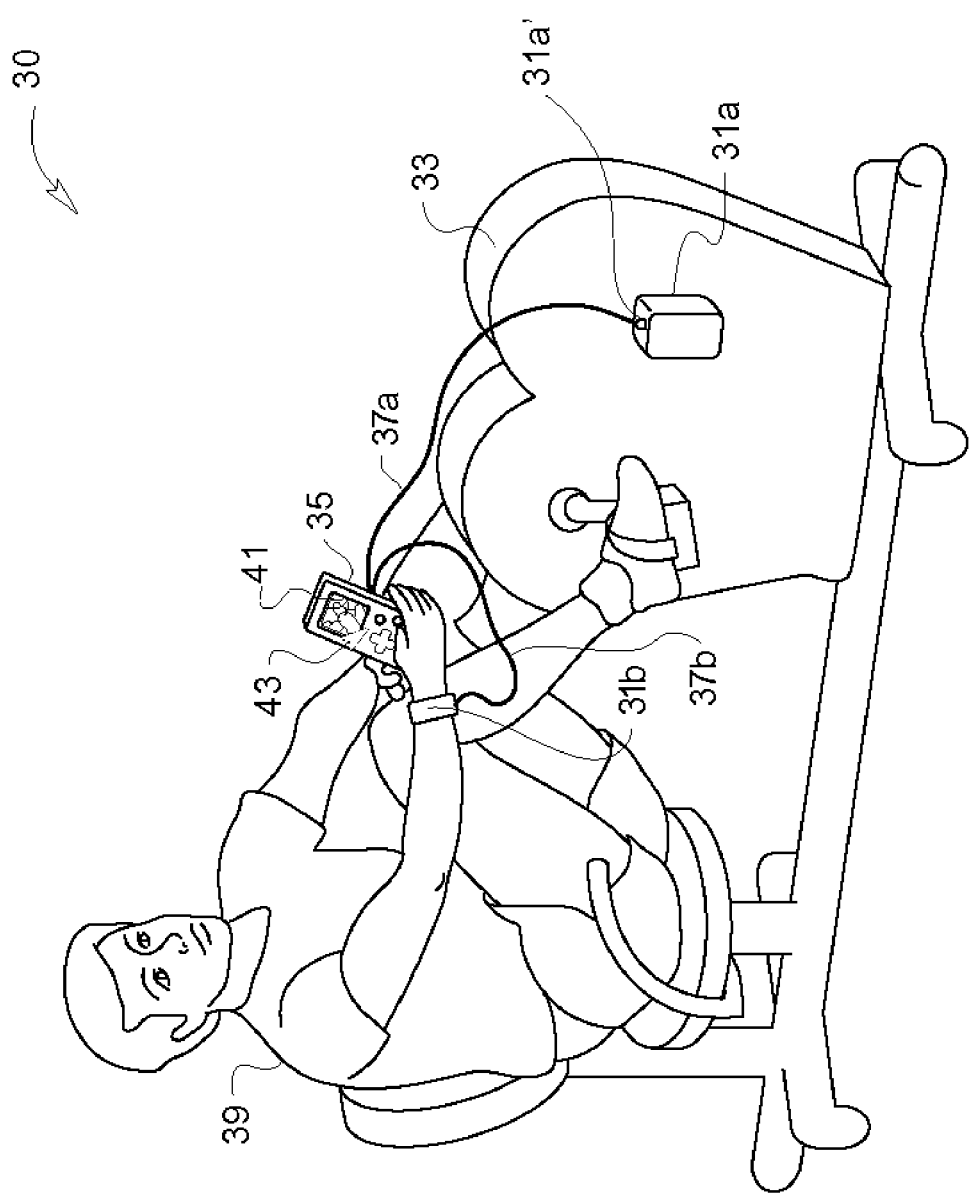
FIG. 2 is a schematic view of an exercise system configured in accordance with a second embodiment of U.S. Pat.

FIG. 2 is a schematic view of an exercise system 30 configured in accordance with a second embodiment of U.S. Pat. No. 5,947,868. With reference to FIG. 2, the exercise system 30 comprises an exercise monitor 31a connected to a recumbent bicycle 33, and a hand-held video game player 35 (such as a GameBoy™ marketed by Nintendo) coupled to an output 31a' of the exercise monitor 31a via a first cable 37a.

The exercise monitor 31a is configured to measure the pedal rate of an exerciser 39 riding the recumbent bicycle 33, and to output an approximately real-time measure of pedal rate via the output 31a'. In addition to the exercise monitor 31a, an exercise monitor 31b is shown connected to the exerciser 39 and to the hand-held video game player 35 via a second cable 37b. The exercise monitor 31b is configured to measure the pulse rate of the exerciser 39. The pedal rate output by the monitor 31a and the pulse rate of the exerciser 39 output by the monitor 31b are monitored by the hand-held video game player 35 while the hand-held video game player 35 runs a video game such as a martial arts video game (represented in FIG. 2 by a martial arts character 41). The exerciser 39 is shown holding the hand-held video game player 35 and can control the kicking, punching and other movements of the martial arts character 41 via buttons 43 on the front of the hand-held video game player 35.

In operation, as the exerciser 39 pedals the recumbent bicycle 33, the monitor 31a measures and outputs a signal representative of the pedal rate of the exerciser 39, and the monitor 31b measures and outputs a signal representative of the pulse rate of the exerciser 39. The pedal rate signal output by the monitor 31a is monitored by the hand-held video game player 35 and is used to control the striking force of the martial arts character 41. The pulse rate signal output by the monitor 31b is monitored by the hand-held video game player 35 and is used to control the energy level of the martial arts character 41. Accordingly, the harder the exerciser 39 pedals the bicycle 33, the harder the martial arts character 41 can strike an opponent. However, the higher the pulse rate of the exerciser 39, the lower the energy level of the martial arts character 41, making the martial arts character 41 more susceptible to attack. By using the monitored performance levels of the exerciser 39 in this manner, to obtain higher and higher game scores, the exerciser 39 must become more and more cardiovascularly fit so that the exerciser 39 can pedal faster while maintaining a lower pulse rate. Cardiovascular fitness becomes a desirable goal of the exerciser 39 because such fitness yields immediate gratification (e.g., a higher game score).

Numerous additional features may be provided. For instance, the system of the '868 Patent (e.g., via computer program code and/or hardware stored in either the computer 15 of FIG. 1 or in the hand-held video game player 35 of FIG. 2) may be configured to (1) at least attempt to prevent an exerciser from overexercising; (2) "reward" an exerciser for exercise performed before and/or after game play on the video game player; (3) "reward" a video game player (e.g., whether the game player is an exerciser) for behavior performed before and/or after game play.

In first aspect, the system of the '868 Patent may be configured to attempt to prevent overexercising by monitoring a pulse rate of an exerciser and by stopping and/or suspending game play if the pulse rate is too high. Alternatively, blood pressure may be monitored. The appropriate pulse rate or blood pressure may be assessed based on age, weight, height, etc., of the exerciser. The video game player may be provided with any suitable interface for receiving information regarding pulse rate, blood pressure, the exerciser (e.g., age, weight, height, etc.) such as a keyboard interface, an infrared or other wireless interface, a serial or parallel cable interface, a USB connection interface, a mouse interface, a light pen interface, a network/Ethernet interface, an Internet interface, a dial-up connection interface, etc. Any other parameter or technique may be used to prevent/reduce overexercising such as monitoring time of exercise, number of steps climbed (e.g., for a stair climber), distance traveled (e.g., for a stationary bicycle or treadmill), or the like.

In a second aspect, an exerciser is rewarded after exercise is performed. For example, an exerciser may be provided with a "smart monitor" which monitors a performance level of exercise (e.g., pedal rate, step rate, length of exercise, pulse rate during exercise, or some other characteristic of exercise) and creates an "indicator" of the performance level. The indicator may be a code (e.g., an encrypted code) that is displayed to the exerciser, and that the exerciser may then provide to the video game player (e.g., via a keyboard, a light pen, via some other device such as a personal computer that couples to the video game player). Based on the code, the video game player "adjusts" the performance level of a video game character in a manner similar to that described in the '868 Patent. In general the video game may be affected in any way by the code (e.g., which is a measure of exercise performance level). Thus, by improving video game character performance based on the code, an exerciser is rewarded for exercise performed before video game play.

Note that the use of a code is not required. The video game player itself may monitor exercise level for use during subsequent game play. For example, Joe may take a hand-held video game player (configured in accordance with the present invention) to a local gym, and may use the video game player to monitor his exercise level while running on a treadmill. The video game player may be provided with a clamp that holds the player on a rail of the treadmill or some other location. During exercise, the video game player may display conventional exercise information such as pulse rate, distance traveled, etc. After exercise, based on the exercise performance level of Joe, the video game player may "adjust" or otherwise affect the performance level of a video game character. Numerous options may be provided. For example, Joe may start a video game (before or during exercise), and the video game player may freeze or suspend play until Joe performs some required level of exercise (e.g., runs faster, cycles for 5 minutes, achieves a certain heart/pulse rate, etc.). Once Joe achieves the required exercise performance level, game play may be reinitiated. This may occur several times during an exercise session. Alternatively, video game character performance may only be affected after Joe has completely finished exercising.

As an additional feature, information regarding performance level of exercise may be communicated to a third party such as an insurance company, a medical facility, a weight loss clinic or any other relevant party. The third party may offer additional incentives for performing exercise (e.g., reduced insurance deductibles, free physicals, etc.), and may even set the performance level requirements for an exerciser (e.g., by programming the video game player, such as via a network like the Internet, via e-mail, etc.).

In a third aspect of the invention, a person is rewarded with improved video game play for non-exercise type activities. For example, game play may be enhanced (e.g., the performance level of a video game player may be improved) if a person (1) achieves a certain grade on a test, completes an education program or studies for a predefined time period; (2) eats at (visits) a certain restaurant (e.g., McDonalds); (3) completes a survey (e.g., by logging on to a Web site and completing the survey); (4) subscribes to a service (e.g., by switching to a certain long distance carrier or by agreeing to a magazine subscription); and/or (4) performs any other predefined task.

Another possible feature includes allowing a person to restart a video game that had previously ended (e.g., because a video game character was "killed") based on a subsequently performed task. Exemplary tasks include, exercising, achieving a certain grade, eating at (visiting) a certain restaurant, completing a survey, subscribing to a magazine, etc.

In some embodiments, it may be desirable to track athletic progress in addition to video game progress and/or correlate video game character performance levels, as discussed above, with achievement of monitored exerciser performance levels. Accordingly, an exercise program may be configured for use with the exercise system 10. The exercise program may be implemented by incorporating a training or exercise regimen into an existing video game or may be implemented by creating a fitness video game. In this way, the exerciser 19 may be able to work toward measurable fitness goals while playing one or more video games.

The training or exercise regimen for use with the exercise system 10 may be designed to guide the exerciser 19 to achievement of a measurable and/or specific goal (e.g., completion of an international distance triathlon, qualifying for the Boston Marathon, etc.) by completing certain workouts while playing one or more video games. These workouts may vary (e.g., in intensity, duration, etc.) in accordance with training methods, such as periodization, over the course of a training regimen and may be completed while playing one or more video games. Additionally, the workouts may require one or more measured exercise performance levels as an input or standard (e.g., a certain measured performance level must be attained). Similarly, the training or exercise regimen may be structured for general fitness without a specific goal. The training or exercise regimen may also be structured to guide the exerciser 19 in a weight loss program or to achieve any other fitness goal.

The training or exercise regimen may be a pre-determined training program which may be included as part of one or more video games or may be available for use with any video game the exerciser selects. For example, a 16 week winter sports shape-up program may be provided in conjunction with a snowboard racing video game or an 18 week first-time marathon training program may be used with a racecar driving video game already commercially available.

Other training programs and/or video games may be used. In some embodiments, the pre-determined training programs may be semi-customizable by the exerciser 19 to allow the exerciser 19 to vary certain parameters of workouts according to their workout and/or gaming preferences. In still other embodiments, the training or exercise regimen may be fully-customizable by the exerciser 19. That is, the exerciser 19 may be able to enter their own training regimen via hand-held video game player 35 or any other suitable input device. This training regimen may be stored (e.g., similar to and/or with game data of a commercially available video game) for use in future workouts.

Additionally, the training program may automatically be changed and/or updated based on the athletic performance of the exerciser 19. For example, if the exerciser is unable to maintain a pre-set cadence on a particular cycling workout, the training regimen may be adjusted to make one or more future workouts more attainable, thus allowing the level of gaming to increase even as athletic performance stagnates or decreases, which may help keep the exerciser 19 interested in continuing the program.

In the same or other embodiments, the training or exercise program may be a log program. That is, information corresponding to measured exercise performance levels (e.g., distance traveled, time, heart rate, etc.) may be logged to a performance chart. This performance chart may be used to provide feedback to the user, to control current and/or future video game character performance levels, and/or may be incorporated into an existing video game or newly created fitness video game. This information may be stored at the video game player 35, the exercise monitor 11, the computer 15, on computer readable medium associated with video game play, or by any other appropriate device or method.

The training or exercise regimen may allow outside information to be inputted (as discussed above) and used in association with video game play. Exemplary information may include calories consumed by the exerciser, information downloaded from other training performance devices (e.g., heart rate ("HR") monitor, GPS monitor, power meter, etc.), and/or any other appropriate information. This outside information may be incorporated into the training or exercise regimen and may be used to affect video game character performance levels. For example, the exerciser 19 may indicate that he/she has consumed 3000 calories, which may exceed a pre-determined calorie consumption limit. Accordingly, the video game character may appear graphically as bloated, lifeless and/or lethargic and/or may have a lower striking force or other performance characteristic. Other graphic and/or video game performance representations of exercise and/or lifestyle performance may be available in one or more video games (e.g., real world injuries or other limitations of an exerciser may be mimicked within a video game).

The training or exercise program and/or associated video game (and/or monitor) may monitor one or more exerciser performance levels during exercise and video gaming sessions. These exerciser performance levels may include HR, cycling pedal rate (cadence), running cadence, cycling power exerted (wattage), pace, time elapsed, oxygen consumption ($VO_2$), blood lactate levels, metabolic rates, etc. Similarly, the exercise system 10 may measure performance levels relative to certain pre-determined training zones (e.g., HR zones, lactate threshold, aerobic threshold ("AeT"), anaerobic threshold ("AT"), etc.). For example, the exerciser 19 may input or dynamically determine a number (typically about five) of HR zones which correspond to a certain target performance level (e.g., the aerobic zone for a particular exerciser may be from 150 to 164 beats per minute ("BPM")) and the exercise program and/or video game may determine video game character performance levels based on which zone the exerciser 19 is exercising in.

Any appropriate method for capturing data related to exerciser performance levels may be used. For example, HR may be determined through a wrist cuff (e.g., monitor 31b), an ear clip, or a wireless chest strap. The exercise system 10 may be capable of capturing data from non-exclusive monitors such as a Polar F11 manufactured by Polar Electro Inc. of Lake Success, N.Y. In this non-limiting example, data (e.g., HR and/or calories burned) from either the chest strap or wrist unit may be downloaded to the exercise system 10 to provide HR information. Similarly, in a cycling workout, an outside monitor such as the Polar 725X, manufactured by Polar Electro Inc. of Lake Success, N.Y., may be used to capture cadence, speed, time elapsed, power, distance traveled, HR, etc. and/or the like. Such information may be transferred to the exercise system 10 via infrared, wireless or wired transmission, or via any other appropriate method. This or other monitors may be used in conjunction with stationary or other fixed exercise equipment (or no exercise equipment) and/or may be used apart from the gaming environment and the information may then be downloaded to the gaming system for logging and/or updated video game character performance levels and/or capabilities. In certain embodiments, the exercise equipment (e.g., recumbent bicycle 13) may be capable of capturing appropriate information.

The individual exerciser performance levels may be inter-related naturally (e.g., as cadence increases, generally HR increases) and the combination of this information may be used to determine a total and/or average performance level. The total and/or average performance level may be used to provide a total and/or average video game character performance level available. Similarly, the individual performance levels may be logged and/or considered separate from each other. In this way, a particular exerciser performance level may correspond to a particular video game character performance level (e.g., HR corresponds to character life level and cadence corresponds to striking force).

Exerciser performance levels as discussed above may control or influence current or future video game character performance levels. These video game character performance levels may include speed, power, strength, life force, striking force, energy level, endurance, skill level, or any other video game character characteristic. Other video game characteristics may be affected such as landscapes, scenery, etc. (e.g., landscape appearances such as color, size, etc., and/or different scenes may be displayed based on exerciser performance levels). In accordance with the training regimen discussed above, the exerciser may be rewarded (e.g., with video game character performance) by following the prescribed workout. For example, if the workout is a 60 minute cycling session at a cadence of 85-95 RPM and a HR in the aerobic zone, the video game character performance levels may be increased in 10 minute increments as long as the cadence and HR remain at the prescribed levels (e.g., the video game character may gain additional striking force without an increase in cadence from the exerciser). However, if the exerciser exceeds or fails to reach exerciser performance levels, there may be deleterious effects on the video game character. For example, if the exerciser progresses into the anaerobic HR zone, the video game character may gain speed or striking force for a very short duration, but then may be affected adversely (e.g., the character may pass out or vomit). Exerciser performance levels may affect video game performance globally and/or locally. In an exemplary football video game, the cadence of the exerciser may affect the arm strength of the quarterback while the HR may affect the speed of the rest of the offense. These may have an inverse relationship such that increasing cadence will increase quarterback arm strength, but the natural by-product of this (increased HR) may cause the remaining offensive players to slow down. Any interrelations between exerciser and video game performance levels may be used and in some embodiments may be scalable and/or controllable by the exerciser 19.

To further encourage continued exercise and adherence to the training regimen, the video game may be limited by the training regimen. The exerciser may be required to complete certain workouts and/or maintain certain exerciser performance levels for the game to progress beyond certain levels. In this way, fitness goal achievement is related back to the video game with increased video game character lives, skills, abilities, guns, available levels, etc. and gaming level advancement or supply procurement may be limited by failure to reach fitness goals. Goal achievement and reward may be for a particular workout session or any future workout, depending on game configuration. In some embodiments, feedback related to exerciser performance levels may be relayed in real time from the input (e.g., monitor) devices to the video game system to immediately affect video game character performance levels. In the same or other embodiments, this feedback may be used to affect future performance in the same or another workout and/or gaming session.

The training program and exercise gaming system described herein may be employed on or with any number of fitness apparatus (or with no fitness apparatus). For example, the exerciser 19 may pedal a recumbent bicycle 13, a stationary upright cycle, a spin bike, or a bicycle attached to a resistance unit. The exerciser may also use an advanced bicycle ergometer such as the Velotron, manufactured by RacerMate, Inc. of Seattle, Wash. or in association with other hardware and/or software fitness packages such as the CompuTrainer, manufactured by RacerMate, Inc. of Seattle, Wash. For example, the exercise program may utilize information provided by the CompuTrainer to create a racing or other game which is separate from the CompuTrainer software but has the same performance characteristics (e.g., speed, intensity, resistance, etc.). The exercise system 10 and training program of the present invention may be compatible so as to download information provided from these or other systems to update the training program and/or current or future video game performance levels. The exerciser 19 may be able to play one or more video games as discussed above while using these fitness apparatus. Similarly, the exerciser may employ the hand-held video game player 35 while using a stair climber or stepper, a treadmill, or any other similar exercise equipment. In some embodiments, workouts performed outside of the gaming environment may be inputted into the exercise system to enhance the training program and/or video game performance levels. This information may be inputted manually (e.g., through the video game player 35) or downloaded from a performance measuring device (e.g., the Polar 725X discussed above).

In some embodiments, an exerciser may be part of a group of exercisers (exercise group 300) that communicate exercise and/or gaming data to other exercisers within the group utilizing a network (an "exercise" network). In this way, exercisers may have access to exercise and/or gaming information, preferably in real time, of other exercisers in the group 300. Exercisers may, for example, be part of an exercise group that has a goal of following an exercise program or achieving a gaming goal as discussed above. While four exercisers are shown in FIG. 3, it will be understood that fewer or more exercisers may be included in the group 300. Additionally, all members of the group 300 may perform the same or different exercises.

As seen in FIG. 3, exercisers 302, 304, 306, and 308 may be connected to exercise network 310. Exercisers 302, 304, 306, 308 may each connect to the exercise network 310 via any suitable means. For example, the exercisers 302, 304, 306, 308 may each be equipped with a wireless device 312a-d capable of transmitting information to the other devices within the exercise group 300 (e.g., over the exercise network 310). Such devices may be, for example, cellular telephones, web-enabled devices such as web-enabled cellular telephones or PDAs, portable web browsers, cellular or web-enabled wrist watches, web-enabled or otherwise portable gaming devices, or any other suitable devices.

The exercise network 310 may include the Internet, a local network (e.g., an intranet), a cellular telephone network, or any other suitable network. The exercise network 310 may be capable of receiving, transmitting, storing, compiling, logging, tabulating, and/or analyzing exercise and/or gaming information received from wireless devices 312a-d (e.g., via one or more servers coupled to the exercise network 310, not shown). Members of the exercise group 300 and/or the exercise network 310 may be a collection of friends, training partners, or may be strangers with similar fitness and/or gaming goals. The exercise group 300 and/or exercise network 310 described herein may encompass any number of people who may have any level of commonality. In some embodiments, private networks may be constructed for a group training for a specific event, for example. In other embodiments, a public network may be constructed which allows anyone to join and track others' performance even if they have disparate fitness goals.

In an exemplary operation, exercisers 302, 304, 306, 308 may be part of a support group for friends trying to lose weight. The exercisers 302, 304, 306, 308 may share information such as caloric intake, intensity and duration of exercise, and/or performance levels. The exercisers 302, 304, 306, 308 may also utilize the exercise network 310 to communicate and offer advice, encouragement, and support.

For example, exerciser 302 may walk frequently and use a pedometer equipped with a wireless device 312a (e.g., a pedometer equipped cellular telephone, a pedometer that communicates wirelessly to a cell phone or PDA, etc.). Information regarding number of steps taken throughout the day may be transmitted to the exercise network 310 and may be made available to other users in any usable form.

Exerciser 304 may ride a recumbent bicycle 314 while playing a video game, as discussed above. The hand-held video game player used by exerciser 304 may also serve as a wireless device 312b and may transmit exercise and/or gaming data to the exercise network 310. The wireless device 312b may also receive information about the performance levels of exerciser 302. For example, the wireless device may convert the number of steps taken by exerciser 302 into a distance traveled and may overlay that information on a map to show exerciser 304 the current location of exerciser 302. Additionally or alternatively, the exercise performance levels of exerciser 302 may be converted to a gaming performance level of a monster or other opponent in the video game played by exerciser 304 or may serve to make the video game more difficult in some way. Additionally or alternatively, the exercise performance levels of exerciser 302 may assist the gaming of exerciser 304 by adding power, striking force, etc. Any other appropriate method to convey the exercise performance levels of exerciser 302 may be used, such as graphical, numerical, or tabular.

Exerciser 306 may jog for fitness and may record his HR with a HR monitor that is also wireless device 312c or may be transmitted to a separate wireless device 312c, depending on use and configuration. Information about exerciser 306's HR may be transmitted to the exercise network 310 and in turn to other users of the network. Exerciser 306 may also receive periodic or constant updates regarding the exercise performance levels of exercisers 302, 304, 308 and may be able to track his performance directly against his friends' performance.

Exerciser 308 may also ride a recumbent bicycle 316 and may carry only a wireless device 312d, which may be a cellular telephone, BlackBerry™, Treo™, pager, or other similar device. Exerciser 308 may transmit exercise performance levels from a performance measuring device to the wireless device 312d (which, in some embodiments, may be the same device), which in turn transmits the information to the exercise network 310. As the exerciser 308 receives information (e.g., in real time) about the walking, riding, and running of exercisers 302, 304, 306, he may be able to transmit encouragement and support to the exercise group's members. In some embodiments, exerciser 308 may use the wireless device 312d to text message (e.g., via short message service "SMS" or instant message "IM") supporting messages to other exercisers, record video and/or audio messages to be transmitted, and/or call exercisers 302, 304, 306 individually or as a group. Exerciser 308 may be prompted to offer support when another exerciser reaches a predetermined gaming and/or exerciser performance level or may simply choose to send a "You go girl!" text message unprompted. Exercisers connected to the exercise network 310 may also be able to continuously communicate using an instant messaging service or group chat room to facilitate quicker transmission and response. Any wireless device 312a-d and/or other performance measuring device may be configured so as to be capable of sending and/or receiving text, audio, video, charts, graphs, and/or any other appropriate exercise, gaming, and/or support information.

Exercisers 302, 304, 306, 308 may enter outside information into wireless devices 312a-d, such as caloric intake, to be transmitted to the exercise network 310 and/or other users. Users may connect to the exercise network 310 via wireless devices 312a-d, personal computers and/or the like and may input information that may be useful or interesting. This information may be made available to other exercisers by transmissions to wireless devices 312a-d, email, display on an editable community web page, or any other suitable information deployment means. Accordingly, users of an exercise network 310 may have real-time and/or historical information available that may include performance level statistics, exercise meeting times and locations, current exercise being performed, caloric intake, weight loss progression, and the like.

Exercisers 302, 304, 306, 308 may also be capable of construction a graphical interpretation of themselves to be available for view by other exercise network 310 users. Exercisers 302, 304, 306, 308 may input information such as body statistics (e.g., height, weight, build, specific measurements, etc.), hair color, eye color, etc. This information may be used to construct an avatar that others may view when accessing the exercise network 310. In the same or other embodiments, exercisers 302, 304, 306, 308 may use pre-constructed avatars or create their own. Exercisers 302, 304, 306, 308 may be able to view avatars of other exercisers who are currently connected to the exercise network 310 and/or are currently exercising. In this way, exercisers 302, 304, 306, 308 may have a visual cue that easily identifies each exerciser and/or that identifies that others may be in need of encouragement. The avatars may be tied to exercise performance levels and/or user input such that they may visually reflect weight loss as determined by direct input or a calculation of caloric intake versus calories burned during exercise. As such, exercisers 302, 304, 306, 308 may be encouraged to send a "Looking fit!" text message without seeing the "real" exerciser.

Though discussed above with regard to four exercisers, it is contemplated that any number of exercisers and/or monitors may connect to an exercise network 310. Additionally multiple exercise networks may be connected (e.g., a local training group may be linked to other local training groups that are part of a national program) and the amount and/or type of information transmitted or received may be modified, restricted, and/or controlled in any suitable manner. Exercisers in an exercise network 310 may join a pre-defined network or may customize it based on their needs. As such, exercisers may have broad access to the network via wireless devices such as cellular phones, PDAs, portable web-browsers, portable video game players, performance measuring devices such as a HR monitoring watch, personal computers, other Internet connections, and the like. Similarly, exercisers may be able to customize the exercise network to form a community in which information is shared in myriad ways (e.g., graphically on wireless devices, in a chart on a website, etc.) so it is more constructive, useful, and/or more readily understandable.

In some aspects of the invention, while interacting in a gaming environment in accordance with one or more of the systems and/or methods described above, an exerciser's game character may be visually transformed in manners indicative of and/or related to the exerciser's real life performance (e.g., exercise performance levels). These transformations may occur instantaneously (e.g., as a direct result of current exercise performance levels) or may be delayed. The transformations may manifest as physical transformations to the video game character and/or fluctuations in video game performance levels, as discussed above. In some embodiments, a combination of these methods may be used.

Physical transformations of an exerciser's video game character may be directly correlated to exercise performance levels. For example, if an exerciser achieves a pre-determined exercise performance level (e.g., cycling cadence greater than 90 RPM) the video game character may "bulk-up" (e.g., appear more massive and/or muscular). The game character's bulk-up may be coordinated with video game performance levels such that achievement of a pre-determined exercise performance level may result in visual transformations as well as improved gaming performance levels (e.g., the character may become 10% more massive and have 10% more striking power). Alternatively, the bulk-up may be only cosmetic or may be correlated such that cosmetic changes are scaled as compared to gaming performance levels. In some embodiments, multiple exercise performance levels and/or gaming performance levels must be achieved to effect a cosmetic change.

Changes in the size and/or appearance of a video game character may occur globally (e.g., to a character's entire body or to all members of a character's team) or may occur locally (e.g., to a single body part or team member). For example, in a team game, such as a war game or sports game, a first exerciser may help a hurt, slow or weak game character of a second exerciser by transferring or "donating" exercise performance level information and/or improved gaming performance level characteristics to the second exerciser and/or to the second exerciser's gaming character. Local changes may be correlated to certain exercise performance levels achieved and/or maintained. For example, an exerciser may be rewarded with a more massive and/or powerful throwing arm when a HR of approximately 170 BPM is maintained. At the same time, the exerciser may be rewarded with greater video game character leg size and/or quickness when a cycling cadence of greater than 90 RPM is maintained. In some embodiments, an exerciser may be penalized for not achieving certain exercise performance goals. Any appropriate correlation between exercise performance levels, video game character performance levels, and visual transformations may be used.

As discussed above with respect to exercise training regimens, an exerciser may vary parameters of exercise (e.g., intensity and duration) over time. Accordingly, particularly during high intensity workouts, it may be desirable to track and/or store exercise performance levels without the exerciser playing a video game. Information related to achieved and/or maintained exercise performance levels may be tracked and recorded for future use. Fluctuations in video game character performance levels and/or appearance changes may thus be exploited in future gaming sessions (e.g., during a lower threshold steady state exercise session or during a sedentary (non-exercise) session). In one exemplary embodiment, a game may pause automatically and require a person to run in place, pedal a bike, jog around the block, etc., to keep a video game character at a certain performance level (e.g., size, striking force, speed, etc.). Exercise performance may be monitored, as previously described.

FIGS. 4A-D illustrate various transformations that a video game character may undergo in response to exercise performance levels in some embodiments of the present invention. These are described for illustrative purposes only and are non-limiting.

Figure 4A:
Figure 4B:

In FIG. 4A, a football quarterback video game character is depicted. This character may be available to an exerciser during game play in accordance with the invention described herein. The quarterback may have certain video game performance levels which may be pre-programmed or may have been previously achieved. For example, the quarterback may initially have an accuracy of 80% for passes within 10 yards, and an accuracy of 40% for passes from 40 to 50 yards. Additionally, the quarterback may initially be a certain size. For example, the video game quarterback may represent a player that is 5'10" tall and weighs 190 pounds. Achievement of certain exercise performance levels may enhance these accuracy ratings and/or character size. For example, if the exerciser completes 90% or more of the exercise sessions of an exercise regimen as described above, the quarterback may improve accuracy by 5% over all throwing ranges and/or grow to 5'11" tall and 205 pounds. In some embodiments, character growth and/or performance levels may be capable of unnatural growth, resulting in characters that appear abnormally large, as depicted in FIG. 4B as compared to the naturally sized video game character of FIG. 4A.

Figure 4C:
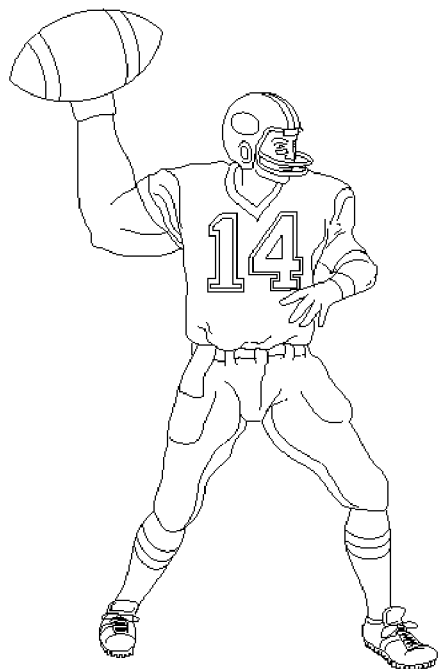

In some embodiments, enhanced character appearance and/or performance levels may not be global. In FIG. 4C, a quarterback is shown with an abnormally sized throwing arm. Achievement of different exercise and/or gaming performance levels may result in such enhancements. For example, an exerciser may be engaged in an exercise program as discussed above. The exercise program may include sprint (e.g., short high-HR, high-cadence) sessions as well as endurance (e.g., long low-HR) sessions. During sprint sessions, exercise performance levels may be tracked, but the exerciser may be unable to play video games. Information indicative of the HR and/or cadence of the exercise session may be recorded and/or transmitted to an exercise network and/or gaming system.

For example, maintaining a cadence of greater than 120 RPM for 10 30-second intervals may be an exercise session goal that, when achieved, results in an increased quarterback arm strength of 50% and a corresponding visual representation thereof. It is noted that alterations in size and video game character performance levels do not have to be directly correlated (e.g., an increase in character arm mass of 50% and strength of 10%).

During a future endurance session and/or during a cool-down period, the quarterback of FIG. 4C may be available for video game play as a reward for achievement of the sprint session goal. In some embodiments, failure to maintain an exercise performance goal (e.g., maximum HR of 140 BPM) during the endurance session may result in the quarterback arm strength and/or size reverting instantaneously or incrementally back to the arm strength and/or size shown in FIG. 4A. In the same or alternative embodiments, achievement of exercise performance goals during the endurance session may have no effect or may improve some aspect of video game character performance levels and/or video game character size.

Figure 4D:

Each exercise performance level may also be correlated to a specific character performance level or body part appearance. For example, during the sprint session described above, the exerciser may earn the improved throwing arm by achievement of the targeted cycling cadence. Separately, maintaining a target HR during the same or other exercise sessions or parts of sessions may result in an increased non-throwing arm strength and/or size as shown in FIG. 4D. This visual enhancement and/or increase in gaming performance levels may enable the quarterback to hold defenders at greater range or slough off more powerful defenders.

While described herein as related to a specific video game character and specific exercise performance levels, it is understood that the games available and/or input provided encompass the gamut of games and exercises available for implementation with the systems and methods described herein. For example, an exerciser may be required to achieve certain exercise performance levels and/or perform outside tasks to cause a character such as Bruce Banner to become The Incredible Hulk™ and increase in size and destructive power in the video game The Incredible Hulk™ Ultimate Destruction produced by Sierra Entertainment, Inc. of Bellevue, Wash. Apparent implementation methods in fighting and sports games are contemplated above, but the appearance transformations available may be non-intuitive as well. For example, achievement of exercise performance levels may enable bulked-up (e.g., steeper, higher, longer, etc.) rollercoasters to be built in RollerCoaster Tycoon 3, manufactured by Atari, Inc. of New York, N.Y.

A first virtual appearance characteristic of a video game character such as arm size, leg size, head size, etc., may change (e.g., disproportionately to other virtual appearance characteristics of the video game character) or be altered during a first time period of exercise, and a second virtual appearance characteristic of the video game character may change or be altered after the first time period of exercise. For example, an exerciser may pedal a bike for a first time period to increase the size of a right arm of a video game character, and then for a second time period to increase the size of a left arm of the video game character, and then for a third time period to increase the size of a right leg of the video game character, etc., until all virtual appearance characteristics of the game character have been enlarged (or reduced). For example, it may be difficult to play a video game while running. However, a heart rate monitor may wirelessly communicate exercise information to a portable game player, such as a cellular telephone, PDA, dedicated game player, etc., while an exerciser is running. By running a first distance, a part of a video game character may increase in size (and/or strength). By then running further, another part of the video game character may increase in size (and/or strength). This may be repeated until multiple video game character virtual appearance characteristics have been enhanced. After exercising, the "enhanced" game character may be used during game play.

In some embodiments, physical characteristics of a video game player may be reflected in or associated with the "virtual" appearance characteristics of a video game character or avatar (e.g., to further customize the video game to the player and exercise). Examples of physical characteristics of the video game player that may be reflected in and potentially altered in the virtual appearance characteristics of a video game character include weight, height, strength, injuries, size, girth, musculature, arm length, dress size, height, age, hair style, charisma, etc. The character may also appear to move faster or slower, appear to be more flexible, appear to be more agile, appear to sweat less, appear to breath more easily, etc. The virtual appearance characteristics may be altered in response to performance of particular exercises associated with certain virtual appearance characteristics or enhancements/alterations of the characteristics. For example, as a player runs on a treadmill, the game character's legs may be altered to appear larger; as the player does push-ups, the game character's arms and chest may be altered to appear more muscular; and as the player swims, the game character may be altered to have a smaller dress size or look younger or appear to be more charismatic. The associations may be based on real world expectations (e.g., if one does push-ups, arm and chest muscles grow) or, in some embodiments, the associations may be exaggerated, arbitrary, opposite, and/or random. Likewise, the enhancements/alterations may be associated with a performance level change in the game and may result in performance level changes that parallel real world expectations (e.g., if the character grows more muscular legs, the character can run faster) or, in some embodiments, the associations may be exaggerated, arbitrary, opposite, and/or random.

Turning now to FIGS. 5 to 10, example process embodiments of the present invention are depicted as flowcharts. The systems discussed above, including the hardware and software components, are useful to perform the methods of the invention. However, it should be understood that not all of the above described components are necessary to perform any of the present invention's methods. In fact, in some embodiments, none of the above described systems are required to practice the present invention's methods. The systems described above are examples of a apparatus embodiments that would be useful in practicing the invention's methods. For example, the exercise monitor 11 described above with respect to FIG. 1 is useful for automatically measuring physical exertion of the user, but it is not absolutely necessary to have such a monitor in order to perform the methods of the invention. In other words, the methods described below may be practiced using, for example, a generic heart rate monitor or by counting pulse beats and a user who simply enters his heart rate or pulse count into the computer 15 (e.g., a video game system such as the Sony® PlayStation 3®).

Referring to FIG. 5, a flow chart is depicted that represents some embodiments of the present invention that may be performed using the systems described above (e.g., FIG. 1) or other devices. It must be understood that the particular arrangement of elements in the flow chart of FIG. 5, as well as the number and order of example steps of various methods discussed herein, is not meant to imply a fixed order, sequence, quantity, and/or timing to the steps; embodiments of the present invention can be practiced in any order, sequence, and/or timing that is practicable.

In general terms and referring to FIG. 5, method steps of an embodiment 500 of the present invention may be summarized as follows. In Step 502, a user goal is determined. In Step 504, one or more user characteristics are determined. In Step 506, a set of activities, or more generally, behaviors, are determined based on the user goal and the user characteristics. The behaviors are determined or selected such that performance of the behaviors will result in the user achieving the user goal. In Step 508, a game is determined, and in Step 510, the game is configured so that successful play of the game requires performing the set of behaviors determined in Step 506.

In the passages that follow, each of these steps will be discussed in greater detail. Note that not all of these steps are required to perform the methods of the present invention and that additional and/or alternative steps are also discussed below. Also note that the above general steps represent features of only some of the embodiments of the present invention and that they may be re-ordered, combined and/or subdivided in any number of different ways so that methods of the present invention include more or fewer actual steps. For example, in some embodiments many additional steps may be added to update and maintain databases that store information about the user, user goals, user characteristics, behavior sets, game parameters, etc., but as indicated, it is not necessary to use such databases in all embodiments of the invention. In other words, the methods of the present invention may contain any number of steps that are practicable to implement the several different inventive processes described herein.

Step 502, determining a user goal, may involve many different sub-processes and may be embodied many different ways. For example, a user may complete a questionnaire or an interview given by a system operator or the computer system. An artificial intelligence program may analyze the user's responses and determine what the user's goal is, for example, in terms of fitness, strength, endurance, stamina, will power, pain tolerance, lung capacity, speed, health, etc. For example, if in response to a series of questions, a user indicates that (1) he wants to participate competitively in a one mile running race, (2) there is an upcoming race scheduled for a future date that he has entered, and (3) a likely winning time would be under four minutes, the system may determine that the user has a "user goal" of being able to run a mile in under four minutes by the future race date. Alternatively, the user may indicate a goal directly by selecting a goal from among a menu of example goals.

Likewise, Step 504, determining user characteristics, may involve many different sub-processes and may be embodied many different ways. As with Step 502, Step 504 may include completing a questionnaire or an interview (given manually or in an automated manner). Alternatively or additionally, sensors may be used to determine various characteristics of the user. For example, a sensor such as a scale may be used to weigh the user. Many other types of sensors may be used. For example, height measurement sensors, heart rate monitors, blood glucose monitors, metabolic rate measuring devices, etc. may be employed.

In some embodiments, the user characteristics may be used to modify the user goal. For example, if the above example user goal is initially determined, but then the system determines that the user weighs 400 pounds, the goal may be adjusted to simply completing the one mile race. In some embodiments, the user may be enabled to override some or all such adjustments or in other embodiments, safety considerations may preclude determining user goals that are dangerous or may endanger the user's health.

Step 506, determining a behavior set, may also involve many different sub-processes and may be embodied many different ways. A set of activities or behaviors are determined that, if performed, will result in the user achieving the user goal. For example, a database of the training effects of various running exercises may be used to determine how much running exercise must be performed over a period of time to improve a person's endurance sufficient to be able to run a mile (user goal). In another example, a database that stores the caloric values of various foods may be used in conjunction with a user's metabolic rate (user characteristic) to determine an exact menu of foods that are to be consumed over a period of time in order to lose a specific amount of weight (user goal). Note that the behavior set is determined based on the user goal and the user characteristics.

Step 508, determining a game, may include allowing the user to select a game from among a number of choices, the system may select a game that has characteristics that make the game suitable for use with encouraging the user to perform the behavior set, or a combination of both. For example, if the behavior set includes performing an exercise routine for a fixed amount of time (e.g., half an hour) each day, the game may be a story based video game that unfolds in, e.g., half hour increments. The half hour story segments may be designed to each end with "cliff hanger" situations that compel the user to return to the game the next day. In another example, if the behavior set includes performing an extended activity, the games that the user may select from may include video games that can be played continuously and indefinitely.

In some embodiments, the game may be completely unrelated to the behavior set. Alternatively, in some embodiments, the game may mimic the behavior set, the user goal, and/or the user's efforts to achieve the user goal. For example, the game selected for a user training to run a four minute mile might be a running race video game. Likewise, the game may include characteristics or configurable parameters that mimic the user characteristics. For example, if the user has an injured ankle (user characteristic), a video game character may have an injured ankle that impacts the user's performance in the running race game.

Step 510, configuring the game, may include setting configurable parameters of the game such that successful play of the game requires performance of the behavior set. In other words, for example, if the behavior set includes maintaining a heart rate within a certain range for a fixed time while walking on a treadmill, a video racing game may allow a user's character to obtain a maximum speed when the heart rate is within the certain range and may slow down the character when the user's heart rate is outside (e.g., above or below) the certain range.

Turning to FIG. 6, an alternative embodiment of the above described method 500 is depicted. In Step 602 of the method 600, input indicating an objective for a user is received. In Step 604, input indicating a characteristic of the user is received. In Step 606, exercise regimen is determined that is designed to cause the user to achieve the objective when the exercise regimen is followed. In Step 608, a video game is determined in which successful play of the video game requires performing the exercise regimen. The video game may include a game system adapted to monitor the user and to influence game play based upon the user performing the exercise regimen.

Turning to FIG. 7, an alternative embodiment of the above described method 600 is depicted. In Step 702 of the method 700, input indicating an objective for a user is received. In Step 704 a characteristic of the user is determined. In Step 706, an exercise regimen designed to cause the user having the determined characteristic to achieve the objective is determine. In Step 708, a game is determined in which successful play of the game requires performing the exercise regimen. In Step 710, the user is monitored during the exercise regimen and/or at other times. In Step 712, game play is influenced based upon the user performing the exercise regimen. The method 700 may also include querying the user about user objectives, receiving an indication of a desired physical characteristic that the user wants to achieve, determining an amount and type of physical activity that the user would need to perform to alter a body of the user to achieve the desired physical characteristic, and sensing physical aspects of the user using one or more sensors. The video game may be adapted to operate in response to signals, indicative of user activity, from sensors adapted to monitor the user. The parameters may include duration, level, frequency, etc. Monitoring the user may include detecting physical characteristics of the user using sensors and influencing game play based upon the user performing the exercise regimen may include improving user performance in the game if the user performs the exercise regimen.

FIG. 8 is a flowchart of an exemplary method 800 for implementing an exercise program in accordance with an embodiment of the present invention. In some embodiments, completion of the video game (e.g., winning the video game, doing well at the video game or achieving a predetermined result, etc.) requires the user to obtain the objective(s) of an exercise program (e.g., being able to run a marathon, losing a predetermined amount of weight, etc.). With reference to FIG. 8, in step 801, an exercise program is determined (e.g., running an international distance triathlon, qualifying for the Boston or another marathon, a first-time marathon training program, a sports shape-up program, a weight loss program, a cardio-strengthening program, or any other exercise program).

In some embodiments, a manufacturer may wish to provide one or more exercise programs for use with a video game. Alternatively or additionally, a user of a video game may wish to associate an exercise program with the video game. For example, the user may specify the exercise program (e.g., as a stated goal of weight loss, distance and/or time to walk, run, bike, etc., or as any other stated goal). Likewise, a video game may include a list of exercise programs available to the user, and allow the user to select (and/or customize) one of the exercise programs. As one particular example, at start-up, a video game may provide a list of exercise programs that may be associated with the video game (e.g., weight loss, distance training, sprint training, etc.). A user of the video game may select one of the exercise programs and specify additional parameters for the exercise program such as how much weigh to loose and/or over what period of time, whether the distance training is for a 5K, 10K or 26K run and/or how fast the run should be completed, etc.

In step 802, a video game for use in achieving the exercise goal is determined. (Note that in some embodiments, step 802 may occur before step 801). The video game may be determined based on the exercise program determined in step 801 (e.g., a marathon training exercise program may be well suited to a battle-field video game in which a video game character runs great distances across a battle field). Alternatively, the video game may be determined based on other criteria such as user preferences, user characteristics (e.g., age, weight, gaming skills, gaming experience, etc.) or the like. In some embodiments, a video game player may provide a list of video games to a user, and allow the user to select a video game from the list.

In step 803, one or more properties of the video game to modify are determined. For instance, the video game and/or game player may have one or more properties of the video game that may be varied to assist in achieving the exercise program determined in step 801. Exemplary properties include character speed, size, life, striking force, energy level, accuracy, etc., game level, game topography, or the like. In some embodiments, such properties may be "controllable" based on an exercise level of the video game player (e.g., pedal rate, step rate, row rate, running rate, pulse rate, distance traveled, time exercised, etc.) as previously described.

In step 804, the one or more properties determined in step 803 are modified (e.g., correlated with or otherwise made dependent on exercise or other activities of the video game player). In one or more embodiments, physical characteristics of a video game player may be reflected in the "virtual" appearance characteristics of a video game character (e.g., to further customize the video game with the exercise program). Examples of physical characteristics of the video game player that may be reflected in the virtual appearance characteristics of a video game character include weight, height, strength, injuries, size, girth, musculature, arm length, dress size, height, age, hair style, charisma, etc. The character may also appear to move faster or slower, appear to be more flexible, appear to be more agile, appear to sweat less, appear to breath more easily, etc.

FIG. 9 is a flowchart of an exemplary method 900 for implementing an exercise program in accordance with an embodiment of the present invention. In some embodiments, completion of the video game (e.g., winning the video game, doing well at the video game or achieving a predetermined result, etc.) requires the user to obtain the objective(s) of an exercise program (e.g., being able to run a marathon, losing a predetermined amount of weight, etc.). With reference to FIG. 9, in step 901, a video game player may provide a list of video game properties available for selection by a user. The selectable video game properties may be properties of the video game to vary to assist in achieving an exercise program.

In step 902, a user may select one of the listed properties. For instance, a user may select character speed, size, life, striking force, energy level, accuracy, etc., game level, game topography, or the like to be "controllable" based on an exercise level of the user during game play (e.g., pedal rate, step rate, row rate, running rate, pulse rate, distance traveled, time exercised, etc.) as previously described.

In step 903, an exercise program is determined (e.g., running an international distance triathlon, qualifying for the Boston or another marathon, a first-time marathon training program, a sports shape-up program, a weight loss program, a cardio-strengthening program, or any other exercise program).

In some embodiments, a manufacture may wish to provide one or more exercise programs for use with a video game. Alternatively or additionally, a user of a video game may wish to associate an exercise program with the video game. For example, the user may specify the exercise program (e.g., as a stated goal of weight loss, distance and/or time to walk, run, bike, etc., or as any other stated goal). Likewise, a video game may include a list of exercise programs available to the user, and allow the user to select (and/or customize) one of the exercise programs. As one particular example, at start-up, a video game may provide a list of exercise programs that may be associated with the video game (e.g., weight loss, distance training, sprint training, etc.). A user of the video game may select one of the exercise programs and specify additional parameters for the exercise program such as how much weigh to loose and/or over what period of time, whether the distance training is for a 5K, 10K or 26K run and/or how fast the run should be completed, etc. In some embodiments, step 903 may occur before step 902.

In step 904, the one or more properties determined in step 703 are modified based on the exercise program (e.g., correlated with or otherwise made dependent on exercise or other activities of the video game player). For example, if the workout is a 60 minute cycling session at a cadence of 85-95 RPM and a HR in the aerobic zone, the video game character performance levels may be increased in 10 minute increments as long as the cadence and HR remain at the prescribed levels (e.g., the video game character may gain additional strike force without an increase in cadence from the exerciser). However, if the exerciser exceeds or fails to reach exerciser performance levels, there may be deleterious effects on the video game character. For example, if the exerciser progresses into the anaerobic HR zone, the video game character may gain speed or striking force for a very short duration, but then may be affected adversely (e.g., the character may pass out or vomit).

FIG. 10 is a flowchart of an exemplary method 1000 for controlling a video game in accordance with a user's exercise objective. With reference to FIG. 10, a exercise level of the user of the video game is monitored (e.g., pulse rate, pedal rate, step rate, running rate, distance traveled, time exercised, etc.). Exemplary monitoring systems are described above.

In step 1002, a determination is made as to which property or properties of the video game are to be affected by the exercise level of the user (e.g., speed, striking force, energy level, accuracy, game level, etc.). In step 1003, the determined property or properties of the video game are modified based on the monitored exercise level and the exercise program. For example, if the workout is a 60 minute cycling session at a cadence of 85-95 RPM and a HR in the aerobic zone, the video game character performance levels may be increased in 10 minute increments as long as the cadence and HR remain at the prescribed levels (e.g., the video game character may gain additional strike force without an increase in cadence from the exerciser). However, if the exerciser exceeds or fails to reach exerciser performance levels, there may be deleterious effects on the video game character.

Any of the above embodiments may be implemented, for example, in the system of the '868 Patent (e.g., via computer program code and/or hardware stored in either the computer 15 of FIG. 1 or in the hand-held video game player 35 of FIG. 2) or in any other suitable system (e.g., a GameBoy Advance, Nintendo DS™, Sony PSP™, a cellular telephone, a PDA, etc.).

The foregoing description discloses only exemplary embodiments of the invention; modifications of the above disclosed apparatus and methods which fall within the scope of the invention will be readily apparent to those of ordinary skill in the art. For instance, any number of performance levels of an exerciser may be monitored and used to control any number of performance levels of a video game character, and the various monitors described herein may communicate with the video game player wirelessly. As well, conditions within a video game may be output by the video game player and used to increase/decrease the difficulty of exercise, or otherwise affect exercise, if so desired. Further, old video games may be modified for use with the present invention, or new video games may be developed.

Additionally, while the present invention has primarily been described with reference to a single exerciser, it will be understood that the invention is equally applicable to multiple exerciser situations. For instance, different video game characters within the same video game may be controlled by different exercisers. That is, the performance level(s) of a first exerciser may control the performance level(s) of a first video game character, while the performance level(s) of a second exerciser may control the performance level(s) of a second video game character contained within the same video game as the first video game character. In this manner, the exerciser who exercises harder will have a gaming advantage over the other exerciser. Such multi-exerciser applications may be performed locally (e.g., all exercisers in the same room) or remotely (e.g., at least one exerciser in a different location who communicates remotely, such as over the INTERNET or the WORLD WIDE WEB). Accordingly, while the present invention has been disclosed in connection with the preferred embodiments thereof, it should be understood that other embodiments may fall within the spirit and scope of the invention, as defined by the following claims.

The invention claimed is:
1. A method, comprising:
monitoring an exercise performance level of a first user, and generating an exercise performance level signal;
providing computer program code executable on a gaming device configured to receive the exercise performance level signal, the computer program code including a video game configured to respond, when executed by the gaming device, to the exercise performance level signal;
generating a game character, by the gaming device, responsive to execution of the video game, wherein the game character has a virtual appearance characteristic based on at least one physical characteristic of the first user;
receiving, by the gaming device, the exercise performance level signal;
altering, by the gaming device, the virtual appearance characteristic of the game character in response to the exercise performance level signal; and
altering, by the gaming device, game play of the video game based on the altered virtual appearance characteristic of the game character,
wherein the video game is executable as part of an exercise group over the Internet that includes the first user and a second user, wherein the first user and second user play the video game, and wherein the method further comprises displaying the game charac- ter to the second user such that the second user can see that the first user has achieved the exercise performance level.

2. The method of claim 1, wherein the game character comprises an avatar representation of the first user.

3. The method of claim 1, wherein generating the game character comprises generating a representation of the first user based on input received from the first user.

4. The method of claim 1, further comprising transmitting the first user's exercise performance level signal to a third party.

5. The method of claim 1, wherein altering the virtual appearance characteristic comprises altering the virtual appearance characteristic to be representative of an effect of performing an exercise.

6. The method of claim 1, wherein altering the virtual appearance characteristic comprises altering a game performance level associated with the virtual appearance characteristic of the game character.

7. The method of claim 6, wherein altering the virtual appearance characteristic comprises altering a second virtual appearance characteristic associated with the altered game performance level.

8. The method of claim 1, wherein altering the virtual appearance characteristic comprises enlarging a muscle size of the game character.

9. The method of claim 1, wherein altering the virtual appearance characteristic comprises increasing a height of the game character.

10. The method of claim 1, wherein the exercise performance level includes a biometric parameter of the first user.

11. An application executable on a wireless device comprising:
a program configured to be stored in the wireless device and that when executed by the wireless device causes the wireless device to:
monitor an exercise performance level of a first user, wherein the exercise performance level includes an exercise performance level signal;
execute a video game configured to respond to the exercise performance level signal;
generate a game character in the video game, wherein the game character has a virtual appearance characteristic based on at least one physical characteristic of the first user;
alter, by the wireless device, the virtual appearance characteristic of the game character in response to the exercise performance level signal; and
alter, by the wireless device, game play of the video game based on the altered virtual appearance characteristic of the game character,
wherein the video game is executable as part of an exercise group over the Internet that includes the first user and a second user, wherein the first user and second user play the video game, and wherein the video game further comprises displaying the game character to the second user such that the second user can see that the first user has achieved the exercise performance level.

12. The application of claim 11, wherein the game character comprises an avatar representation of the first user.

13. The application of claim 11, wherein the program is configured to generate a representation of the first user based on input received from the first user.

14. The application of claim 11, wherein the program is further configured to transmit the first user's exercise performance level signal to a third party.

15. The application of claim 11, wherein the program is configured to alter the virtual appearance characteristic to be representative of an effect of performing an exercise.

16. The application of claim 11, wherein the program is configured to alter a game performance level associated with the virtual appearance characteristic of the game character.

17. The application of claim 16, wherein the program is configured to alter a second virtual appearance characteristic associated with the altered game performance level.

18. The application of claim 11, wherein the program is configured to alter the virtual appearance characteristic by enlarging a muscle size of the game character.

19. The application of claim 11, wherein the program is configured to alter the virtual appearance characteristic by increasing a height of the game character.

20. The application of claim 11, wherein the exercise performance level includes a biometric parameter of the first user.

* * * * *